US010563230B2

(12) United States Patent
Kwon et al.

(10) Patent No.: US 10,563,230 B2
(45) Date of Patent: Feb. 18, 2020

(54) MULTI-ENZYME CONJUGATE, METHOD FOR PREPARING THE SAME AND METHOD FOR PREPARING ORGANIC COMPOUND USING THE SAME

(71) Applicant: Gwangju Institute of Science and Technology, Gwangju (KR)

(72) Inventors: Inchan Kwon, Gwangju (KR); Jinhwan Cho, Gwangju (KR); Sung In Lim, Atlanta, GA (US)

(73) Assignee: GWANGJU INSTITUTE OF SCIENCE AND TECHNOLOGY, Gwangju (KR)

( * ) Notice: Subject to any disclaimer, the term of this patent is extended or adjusted under 35 U.S.C. 154(b) by 31 days.

(21) Appl. No.: 15/606,838

(22) Filed: May 26, 2017

(65) Prior Publication Data
US 2017/0356014 A1    Dec. 14, 2017

(30) Foreign Application Priority Data

May 27, 2016    (KR) .................. 10-2016-0065814

(51) Int. Cl.
| | | |
|---|---|---|
| *C12P 7/24* | (2006.01) | |
| *C12P 7/42* | (2006.01) | |
| *C12N 9/02* | (2006.01) | |
| *C12N 9/14* | (2006.01) | |
| *C12P 7/18* | (2006.01) | |
| *C12P 7/02* | (2006.01) | |
| *C12N 9/96* | (2006.01) | |
| *C12P 13/00* | (2006.01) | |
| *C12N 9/06* | (2006.01) | |
| *C12P 7/40* | (2006.01) | |
| *C12P 41/00* | (2006.01) | |
| *C12P 17/02* | (2006.01) | |
| *C12P 33/00* | (2006.01) | |
| *C12P 7/26* | (2006.01) | |
| *C12N 9/10* | (2006.01) | |
| *C12P 7/46* | (2006.01) | |
| *C12P 13/02* | (2006.01) | |
| *C12N 9/04* | (2006.01) | |

(52) U.S. Cl.
CPC .............. *C12P 7/18* (2013.01); *C12N 9/0006* (2013.01); *C12N 9/0008* (2013.01); *C12N 9/0016* (2013.01); *C12N 9/0036* (2013.01); *C12N 9/0073* (2013.01); *C12N 9/1096* (2013.01); *C12N 9/14* (2013.01); *C12N 9/96* (2013.01); *C12P 7/02* (2013.01); *C12P 7/26* (2013.01); *C12P 7/40* (2013.01); *C12P 7/46* (2013.01); *C12P 13/004* (2013.01); *C12P 13/02* (2013.01); *C12P 17/02* (2013.01); *C12P 33/00* (2013.01); *C12P 41/002* (2013.01); *C12Y 101/01037* (2013.01); *C12Y 102/01002* (2013.01)

(58) Field of Classification Search
CPC ........... C12P 13/001; C12P 7/24; C12P 19/40; C12Y 301/01; C12Y 101/01037; C12N 9/0016
USPC ................................ 435/189, 147, 92, 252.2
See application file for complete search history.

(56) References Cited

FOREIGN PATENT DOCUMENTS

KR    10-1637010 B1    7/2016

OTHER PUBLICATIONS

Devos et al., (Proteins: Structure, Function and Genetics, 2000, vol. 41: 98-107.*
Whisstock et al., (Quarterly Reviews of Biophysics 2003, vol. 36 (3): 307-340.*
Witkowski et al., (Biochemistry 38:11643-11650, 1999.*
Kisselev L., (Structure, 2002, vol. 10: 8-9.*
Sanne Schoffelen et al., "Chemical approaches for the construction of multi-enzyme reaction systems", Current Opinion in Structural Biology, 2013, 23, 613-621 pages.
Adrian H. Elcock et al., "Evidence for Electrostatic Channeling in a Fusion Protein of Malate Dehydrogenase and Citrate Synthase", Biochemistry, 1996, 35, 12652-12658 pages.
Erik Steen Redeker et al., "Protein Engineering for Directed Immobilization", Bioconjugate Chemistry, 2013, 24, 1761-1777 pages.
Josui Shimada et al., "Programmable protein—protein conjugation via DNA-based self-assembly", Chem. Commun., 2012, 48, 6226-6228 pages.
Sanne Schoffelen et al., "Construction of a Multifunctional Enzyme Complex via the Strain-Promoted Azide-Alkyne Cycloaddition", Bioconjugate Chemistry, 2013, 24, 987-996 pages.
Emanuele Ricca et al.,"Multi-Enzymatic Cascade Reactions: Overview and Perspectives", Advanced Synthesis & Catalysis, 2011, 353, 2239-2262 pages.
Sung In Lim et al., "Site-specific albumination of a therapeutic protein with multi-subunit to prolong activity in vivo", Journal of Controlled Release, 2015, 207, 93-100 pages.

(Continued)

*Primary Examiner* — Robert B Mondesi
*Assistant Examiner* — Mohammad Y Meah
(74) *Attorney, Agent, or Firm* — Hauptman Ham, LLP

(57) ABSTRACT

The present disclosure relates to a multi-enzyme conjugate, a method for preparing the same and a method for preparing an organic compound using the same. More particularly, a multi-enzyme conjugate exhibiting improved catalytic efficiency over respective free enzymes using site-specific incorporation of a clickable non-natural amino acid into the enzymes and two compatible click reactions, a method for preparing the same and a method for preparing an organic compound using the same may be provided.

2 Claims, 10 Drawing Sheets

Specification includes a Sequence Listing.

(56) References Cited

OTHER PUBLICATIONS

Sung In Lim et al., "Double clicking for site-specific coupling of multiple enzymes", Chem. Commun., 2015, 51, 13607-13610 pages.

Sung In Lim et al., "Spatially-controlled Albumination of Therapeutic Proteins for the Prolonged Serum Half-life", Symposium, www.kormb.or.kr, Jun. 25.

Inchan Kwon, "Engineering Therapeutic Proteins for the Prolonged Serum Half-Life and Reduced Aggregation", School of Materials Science and Engineering, GIST, 61005.

Sung In Lim et al., "Double clicking for site-specific coupling of multiple enzymes", 30th Anniversary Meeting and International Symposium of KSBB, Songdo Convensia, Incheon, Korea, Oct. 11-14, 2015.

Inchan Kwon et al., "Engineering therapeutic proteins using genetically encoded non-natural amino acids", YABEC 2015 Program, Oct. 14-16, 2015, 16:40-17:00.

Inchan Kwon, "Engineering Therapeutic Proteins and Biocatalysts via Spatially Controlled Chemical Modification", 2015, Fall semester seminar, KAIST.

\* cited by examiner

FIG. 9A

FDH from Thiobacillus sp.

MAKILCVLYDDPVDGYPKTYARDDLPKIDHYPGGQTLPTPKAIDFTPGQLLGSVSGELGLRKYLEANGHTFVVTSDKDGP
DSVFEKELVDADVVISQPFWPAYLTPERIAKAKNLKLALTAGIGSDHVDLQSAIDRGITVAEVTYCNSISVAEHVVMMIL
GLVRNYIPSHDWARKGGWNIADCVEHSYDLEGMTVGSVAAGRIGLAVLRRLAPFDVKLHYTDRHRLPEAVEKELGLVWHD
TREDMYPHCDVVTLNVPLHPETEHMINDETLKLFKRGAYIVNTARGKLADRDAIVRAIESGQLAGYAGDVWFPQPAPKDH
PWRTMKWEGMTPHISGTSLSAQARYAAGTREILECFFEGRPIRDEYLIVQGGALAGTGAHSYSKGNATGGSEEAAKFKKA
GLEHHHHHH

FIG. 9B

MDH from Pseudomonas fluorescens DSM 50106

MKLNKQNLTQLAPEVKLPAYTLADTRQGIAHIGVGGFHRAHQAYYTDALMNTGEGLDWSICGVGLRSEDRKARDDLAGQD
YLFTLYELGDTDDTEVRVIGSISDMLLAEDSAQALIDKLASPEIRIVSLTITEGGYCIDDSNGEFMAHLPQIQHDLAHPS
SPKTVFGFICAALTQRRAAGIPAFTVMSCDNLPHNGAVTRKALLAFAALHNAELHDWIKAHVSFPNAMVDRITPMTSTAH
RLQLHDEHGIDDAWPVVCEPFVQWVLEDKFVNGRPAWEKVGVQFTDDVTPYEEMKIGLLNGSHLALTYLGFLKGYRFVHE
TMNDPLFVAYMRAYMDLDVTPNLAPVPGIDLTDYKQTLVDRFSNQAIADQLERVCSDGSSKFPKFTVPTINRLIADGRET
ERAALVVAAWALYLKGVDENGVSYTIPDPRAEFCQGLVSDDALISQRLLAVEEIFGTAIPNSPEFVAAFERCYGSLRDNG
VTTTLKHLLKKPVHHHHHH

SEQUENCE LISTING

```
<160> NUMBER OF SEQ ID NOS: 18

<210> SEQ ID NO 1
<211> LENGTH: 406
<212> TYPE: PRT
<213> ORGANISM: Thiobacillus sp. KNK65MA
<220> FEATURE:
<221> NAME/KEY: MISC_FEATURE
<222> LOCATION: (1)..(406)
<223> OTHER INFORMATION: Formate Dehydrogenase (FDH)

<400> SEQUENCE: 1

Gly Ala Met Gly Ser Met Ala Lys Ile Leu Cys Val Leu Tyr Asp Asp
1               5                   10                  15

Pro Val Asp Gly Tyr Pro Lys Thr Tyr Ala Arg Asp Asp Leu Pro Lys
            20                  25                  30
```

Ile Asp His Tyr Pro Gly Gly Gln Thr Leu Pro Thr Pro Lys Ala Ile
35                  40                  45

Asp Phe Thr Pro Gly Gln Leu Leu Gly Ser Val Ser Gly Glu Leu Gly
50                  55                  60

Leu Arg Lys Tyr Leu Glu Ala Asn Gly His Thr Phe Val Val Thr Ser
65                  70                  75                  80

Asp Lys Asp Gly Pro Asp Ser Val Phe Glu Lys Glu Leu Val Asp Ala
                85                  90                  95

Asp Val Val Ile Ser Gln Pro Phe Trp Pro Ala Tyr Leu Thr Pro Glu
                100                 105                 110

Arg Ile Ala Lys Ala Lys Asn Leu Lys Leu Ala Leu Thr Ala Gly Ile
                115                 120                 125

Gly Ser Asp His Val Asp Leu Gln Ser Ala Ile Asp Arg Gly Ile Thr
130                 135                 140

Val Ala Glu Val Thr Tyr Cys Asn Ser Ile Ser Val Ala Glu His Val
145                 150                 155                 160

Val Met Met Ile Leu Gly Leu Val Arg Asn Tyr Ile Pro Ser His Asp
                165                 170                 175

Trp Ala Arg Lys Gly Gly Trp Asn Ile Ala Asp Cys Val Glu His Ser
                180                 185                 190

Tyr Asp Leu Glu Gly Met Thr Val Gly Ser Val Ala Ala Gly Arg Ile
                195                 200                 205

Gly Leu Ala Val Leu Arg Arg Leu Ala Pro Phe Asp Val Lys Leu His
210                 215                 220

Tyr Thr Asp Arg His Arg Leu Pro Glu Ala Val Glu Lys Glu Leu Gly
225                 230                 235                 240

Leu Val Trp His Asp Thr Arg Glu Asp Met Tyr Pro His Cys Asp Val
                245                 250                 255

Val Thr Leu Asn Val Pro Leu His Pro Glu Thr Glu His Met Ile Asn
                260                 265                 270

Asp Glu Thr Leu Lys Leu Phe Lys Arg Gly Ala Tyr Ile Val Asn Thr
                275                 280                 285

Ala Arg Gly Lys Leu Ala Asp Arg Asp Ala Ile Val Arg Ala Ile Glu
290                 295                 300

Ser Gly Gln Leu Ala Gly Tyr Ala Gly Asp Val Trp Phe Pro Gln Pro
305                 310                 315                 320

Ala Pro Lys Asp His Pro Trp Arg Thr Met Lys Trp Glu Gly Met Thr
                325                 330                 335

Pro His Ile Ser Gly Thr Ser Leu Ser Ala Gln Ala Arg Tyr Ala Ala
                340                 345                 350

Gly Thr Arg Glu Ile Leu Glu Cys Phe Phe Glu Gly Arg Pro Ile Arg
                355                 360                 365

Asp Glu Tyr Leu Ile Val Gln Gly Gly Ala Leu Ala Gly Thr Gly Ala
                370                 375                 380

His Ser Tyr Ser Lys Gly Asn Ala Thr Gly Gly Ser Glu Glu Ala Ala
385                 390                 395                 400

Lys Phe Lys Lys Ala Gly
                405

<210> SEQ ID NO 2
<211> LENGTH: 493
<212> TYPE: PRT
<213> ORGANISM: Pseudomonas fluorescens
<220> FEATURE:
<221> NAME/KEY: MISC_FEATURE
<222> LOCATION: (1)..(493)
<223> OTHER INFORMATION: Mannitol Dehydrogenase (MDH)

<400> SEQUENCE: 2

| | | | | | | | | | | | | | | |
|---|---|---|---|---|---|---|---|---|---|---|---|---|---|---|
| Met | Lys | Leu | Asn | Lys | Gln | Asn | Leu | Thr | Gln | Leu | Ala | Pro | Glu | Val | Lys |
| 1 | | | | 5 | | | | | 10 | | | | | 15 | |
| Leu | Pro | Ala | Tyr | Thr | Leu | Ala | Asp | Thr | Arg | Gln | Gly | Ile | Ala | His | Ile |
| | | | 20 | | | | | 25 | | | | | 30 | | |
| Gly | Val | Gly | Gly | Phe | His | Arg | Ala | His | Gln | Ala | Tyr | Tyr | Thr | Asp | Ala |
| | | | 35 | | | | 40 | | | | | 45 | | | |
| Leu | Met | Asn | Thr | Gly | Glu | Gly | Leu | Asp | Trp | Ser | Ile | Cys | Gly | Val | Gly |
| | 50 | | | | | 55 | | | | | 60 | | | | |
| Leu | Arg | Ser | Glu | Asp | Arg | Lys | Ala | Arg | Asp | Asp | Leu | Ala | Gly | Gln | Asp |
| 65 | | | | | 70 | | | | | 75 | | | | | 80 |
| Tyr | Leu | Phe | Thr | Leu | Tyr | Glu | Leu | Gly | Asp | Thr | Asp | Asp | Thr | Glu | Val |
| | | | | 85 | | | | | 90 | | | | | 95 | |
| Arg | Val | Ile | Gly | Ser | Ile | Ser | Asp | Met | Leu | Leu | Ala | Glu | Asp | Ser | Ala |
| | | | 100 | | | | | 105 | | | | | 110 | | |
| Gln | Ala | Leu | Ile | Asp | Lys | Leu | Ala | Ser | Pro | Glu | Ile | Arg | Ile | Val | Ser |
| | | | 115 | | | | | 120 | | | | | 125 | | |
| Leu | Thr | Ile | Thr | Glu | Gly | Gly | Tyr | Cys | Ile | Asp | Asp | Ser | Asn | Gly | Glu |
| | 130 | | | | | 135 | | | | | 140 | | | | |
| Phe | Met | Ala | His | Leu | Pro | Gln | Ile | Gln | His | Asp | Leu | Ala | His | Pro | Ser |
| 145 | | | | | 150 | | | | | 155 | | | | | 160 |
| Ser | Pro | Lys | Thr | Val | Phe | Gly | Phe | Ile | Cys | Ala | Ala | Leu | Thr | Gln | Arg |
| | | | | 165 | | | | | 170 | | | | | 175 | |
| Arg | Ala | Ala | Gly | Ile | Pro | Ala | Phe | Thr | Val | Met | Ser | Cys | Asp | Asn | Leu |
| | | | 180 | | | | | 185 | | | | | 190 | | |
| Pro | His | Asn | Gly | Ala | Val | Thr | Arg | Lys | Ala | Leu | Leu | Ala | Phe | Ala | Ala |
| | | | 195 | | | | | 200 | | | | | 205 | | |
| Leu | His | Asn | Ala | Glu | Leu | His | Asp | Trp | Ile | Lys | Ala | His | Val | Ser | Phe |
| | 210 | | | | | 215 | | | | | 220 | | | | |
| Pro | Asn | Ala | Met | Val | Asp | Arg | Ile | Thr | Pro | Met | Thr | Ser | Thr | Ala | His |
| 225 | | | | | 230 | | | | | 235 | | | | | 240 |
| Arg | Leu | Gln | Leu | His | Asp | Glu | His | Gly | Ile | Asp | Asp | Ala | Trp | Pro | Val |
| | | | | 245 | | | | | 250 | | | | | 255 | |
| Val | Cys | Glu | Pro | Phe | Val | Gln | Trp | Val | Leu | Glu | Asp | Lys | Phe | Val | Asn |
| | | | 260 | | | | | 265 | | | | | 270 | | |
| Gly | Arg | Pro | Ala | Trp | Glu | Lys | Val | Gly | Val | Gln | Phe | Thr | Asp | Asp | Val |
| | | | 275 | | | | | 280 | | | | | 285 | | |
| Thr | Pro | Tyr | Glu | Glu | Met | Lys | Ile | Gly | Leu | Leu | Asn | Gly | Ser | His | Leu |
| | 290 | | | | | 295 | | | | | 300 | | | | |
| Ala | Leu | Thr | Tyr | Leu | Gly | Phe | Leu | Lys | Gly | Tyr | Arg | Phe | Val | His | Glu |
| 305 | | | | | 310 | | | | | 315 | | | | | 320 |
| Thr | Met | Asn | Asp | Pro | Leu | Phe | Val | Ala | Tyr | Met | Arg | Ala | Tyr | Met | Asp |
| | | | | 325 | | | | | 330 | | | | | 335 | |
| Leu | Asp | Val | Thr | Pro | Asn | Leu | Ala | Pro | Val | Pro | Gly | Ile | Asp | Leu | Thr |
| | | | 340 | | | | | 345 | | | | | 350 | | |
| Asp | Tyr | Lys | Gln | Thr | Leu | Val | Asp | Arg | Phe | Ser | Asn | Gln | Ala | Ile | Ala |
| | | | 355 | | | | | 360 | | | | | 365 | | |
| Asp | Gln | Leu | Glu | Arg | Val | Cys | Ser | Asp | Gly | Ser | Ser | Lys | Phe | Pro | Lys |
| | 370 | | | | | 375 | | | | | 380 | | | | |
| Phe | Thr | Val | Pro | Thr | Ile | Asn | Arg | Leu | Ile | Ala | Asp | Gly | Arg | Glu | Thr |
| 385 | | | | | 390 | | | | | 395 | | | | | 400 |

Glu Arg Ala Ala Leu Val Val Ala Ala Trp Ala Leu Tyr Leu Lys Gly
            405                 410                 415

Val Asp Glu Asn Gly Val Ser Tyr Thr Ile Pro Asp Pro Arg Ala Glu
            420                 425                 430

Phe Cys Gln Gly Leu Val Ser Asp Asp Ala Leu Ile Ser Gln Arg Leu
            435                 440                 445

Leu Ala Val Glu Glu Ile Phe Gly Thr Ala Ile Pro Asn Ser Pro Glu
450                 455                 460

Phe Val Ala Ala Phe Glu Arg Cys Tyr Gly Ser Leu Arg Asp Asn Gly
465                 470                 475                 480

Val Thr Thr Thr Leu Lys His Leu Leu Lys Lys Pro Val
            485                 490

<210> SEQ ID NO 3
<211> LENGTH: 256
<212> TYPE: PRT
<213> ORGANISM: Drosophila melanogaster
<220> FEATURE:
<221> NAME/KEY: MISC_FEATURE
<222> LOCATION: (1)..(256)
<223> OTHER INFORMATION: Alcohol Dehydrogenase (ADH)

<400> SEQUENCE: 3

Met Ser Phe Thr Leu Thr Asn Lys Asn Val Ile Phe Val Ala Gly Leu
1               5                   10                  15

Gly Gly Ile Gly Leu Asp Thr Ser Lys Glu Leu Leu Lys Arg Asp Leu
            20                  25                  30

Lys Asn Leu Val Ile Leu Asp Arg Ile Glu Asn Pro Ala Ala Ile Ala
        35                  40                  45

Glu Leu Lys Ala Ile Asn Pro Lys Val Thr Val Thr Phe Tyr Pro Tyr
    50                  55                  60

Asp Val Thr Val Pro Ile Ala Glu Thr Thr Lys Leu Leu Lys Thr Ile
65                  70                  75                  80

Phe Ala Gln Leu Lys Thr Val Asp Val Leu Ile Asn Gly Ala Gly Ile
                85                  90                  95

Leu Asp Asp His Gln Ile Glu Arg Thr Ile Ala Val Asn Tyr Thr Gly
            100                 105                 110

Leu Val Asn Thr Thr Thr Ala Ile Leu Asp Phe Trp Asp Lys Arg Lys
        115                 120                 125

Gly Gly Pro Gly Gly Ile Ile Cys Asn Ile Gly Ser Val Thr Gly Phe
    130                 135                 140

Asn Ala Ile Tyr Gln Val Pro Val Tyr Ser Gly Thr Lys Ala Ala Val
145                 150                 155                 160

Val Asn Phe Thr Ser Ser Leu Ala Lys Leu Ala Pro Ile Thr Gly Val
                165                 170                 175

Thr Ala Tyr Thr Val Asn Pro Gly Ile Thr Arg Thr Thr Leu Val His
            180                 185                 190

Lys Phe Asn Ser Trp Leu Asp Val Glu Pro Gln Val Ala Glu Lys Leu
        195                 200                 205

Leu Ala His Pro Thr Gln Pro Ser Leu Ala Cys Ala Glu Asn Phe Val
    210                 215                 220

Lys Ala Ile Glu Leu Asn Gln Asn Gly Ala Ile Trp Lys Leu Asp Leu
225                 230                 235                 240

Gly Thr Leu Glu Ala Ile Gln Trp Thr Lys His Trp Asp Ser Gly Ile
                245                 250                 255

<210> SEQ ID NO 4
<211> LENGTH: 455
<212> TYPE: PRT
<213> ORGANISM: Streptococcus equi subsp. zooepidemicus ATCC 35246
<220> FEATURE:
<221> NAME/KEY: MISC_FEATURE
<222> LOCATION: (1)..(455)
<223> OTHER INFORMATION: NADH Oxidase (NOX)

<400> SEQUENCE: 4

```
Met Ser Lys Ile Val Val Ile Gly Ala Asn His Ala Gly Thr Ala Cys
1               5                   10                  15

Ile Lys Thr Met Leu Thr Asn Tyr Gly Asp Ala Asn Glu Ile Val Val
            20                  25                  30

Phe Asp Gln Asn Ser Asn Ile Ser Phe Leu Gly Cys Gly Met Ala Leu
        35                  40                  45

Trp Ile Gly Glu Gln Ile Ser Gly Pro Glu Gly Leu Phe Tyr Ser Asn
    50                  55                  60

Lys Glu Glu Leu Glu Ser Leu Gly Ala Lys Val Tyr Met Glu Ser Pro
65                  70                  75                  80

Val Gln Ser Ile Asp Tyr Asp Ala Lys Thr Val Thr Ala Leu Val Asp
                85                  90                  95

Gly Lys Glu His Val Glu Ser Tyr Asp Lys Leu Ile Phe Ala Thr Gly
            100                 105                 110

Ser Gln Pro Ile Leu Pro Pro Ile Lys Gly Ala Glu Ile Lys Glu Gly
        115                 120                 125

Ser Leu Glu Phe Glu Ala Thr Leu Glu Asn Leu Gln Phe Val Lys Leu
    130                 135                 140

Tyr Gln Asn Ser Ala Asp Val Ile Ser Lys Leu Glu Asn Lys Asp Ile
145                 150                 155                 160

Lys Arg Val Ala Val Val Gly Ala Gly Tyr Ile Gly Val Glu Leu Ala
                165                 170                 175

Glu Ala Phe Gln Arg Lys Gly Lys Glu Val Val Leu Ile Asp Val Ala
            180                 185                 190

Asp Thr Cys Leu Ala Gly Tyr Tyr Asp Arg Asp Leu Thr Asp Val Met
        195                 200                 205

Ser Lys Asn Leu Glu Glu His Gly Ile Gln Leu Ala Phe Gly Glu Thr
    210                 215                 220

Val Gln Glu Val Ala Gly Asp Gly Lys Val Glu Lys Leu Ile Thr Asp
225                 230                 235                 240

Lys Asn Glu Tyr Asp Val Asp Met Val Ile Leu Ala Val Gly Phe Arg
                245                 250                 255

Pro Asn Thr Ala Leu Gly Ala Gly Lys Ile Glu Leu Phe Arg Asn Gly
            260                 265                 270

Ala Phe Leu Val Asn Lys His Gln Glu Thr Ser Ile Pro Gly Ile Tyr
        275                 280                 285

Ala Ile Gly Asp Cys Ala Thr Ile Tyr Asp Asn Ala Thr Arg Asp Thr
    290                 295                 300

Asn Tyr Ile Ala Leu Ala Ser Asn Ala Val Arg Thr Gly Ile Val Ala
305                 310                 315                 320

Ala His Asn Ala Cys Gly Thr Ala Leu Glu Gly Ile Gly Val Gln Gly
                325                 330                 335

Ser Asn Gly Ile Ser Ile Tyr Gly Leu His Met Val Ser Thr Gly Leu
            340                 345                 350

Thr Leu Glu Lys Ala Lys Cys Leu Gly Phe Asp Ala Ala Val Thr Glu
```

```
                355                 360                 365
Tyr Thr Asp Asn Gln Lys Pro Glu Phe Ile Glu His Gly Asn Phe Gln
370                 375                 380

Val Thr Ile Lys Ile Val Tyr Asp Lys Glu Ser Arg Arg Ile Leu Gly
385                 390                 395                 400

Ala Gln Met Ala Ser His Glu Asp Ile Ser Met Gly Ile His Met Phe
                405                 410                 415

Ser Leu Ala Ile Gln Glu Glu Val Thr Ile Glu Lys Leu Ala Leu Thr
                420                 425                 430

Asp Ile Phe Phe Leu Pro His Phe Asn Lys Pro Tyr Asn Tyr Ile Thr
                435                 440                 445

Met Ala Ala Leu Gly Ala Glu
                450                 455

<210> SEQ ID NO 5
<211> LENGTH: 331
<212> TYPE: PRT
<213> ORGANISM: Brachyspira hyodysenteriae ATCC 27164
<220> FEATURE:
<221> NAME/KEY: MISC_FEATURE
<222> LOCATION: (1)..(331)
<223> OTHER INFORMATION: Lactate Dehydrogenase (LDH)

<400> SEQUENCE: 5

Met Ser Ile Val Val Tyr Ser Phe Leu Asp Asp Glu Ser Glu Phe Phe
1               5                   10                  15

Lys Leu Met Glu Lys Lys Tyr Asn Thr Lys Phe Thr Leu His Lys His
                20                  25                  30

His Leu Asn Ile Asp Asn Val Lys Asp Ala Glu Gly Phe Asp Ser Val
            35                  40                  45

Val Phe Asn Ala Arg Asp Ala Ile Thr Ser Glu Val Leu Asp Lys Leu
        50                  55                  60

Lys Glu Tyr Gly Val Lys Tyr Met Ser Thr Arg Ser Val Gly Tyr Asp
65                  70                  75                  80

Asn Ile Asp Ile Asp Tyr Ala Asn Lys Ile Gly Ile Lys Ile Ala Asn
                85                  90                  95

Val Pro Ser Tyr Ser Pro Asn Ser Val Ser Glu Phe Thr Ile Leu Ser
                100                 105                 110

Leu Leu Ser Ile Val Lys Asn Tyr Asn Asn Leu Leu Ile Asn Gly Tyr
            115                 120                 125

Asn Arg Asn Tyr Thr Arg Thr Gly Leu Val Ala Lys Glu Ile Arg Asn
        130                 135                 140

Leu Asn Ile Gly Val Ile Gly Thr Gly Arg Ile Gly Ser Leu Thr Val
145                 150                 155                 160

Lys His Leu Lys Gly Phe Ser Pro Lys Asn Ile Phe Val Tyr Ser Arg
                165                 170                 175

Thr Glu Lys Glu Glu Ile Lys Gln Tyr Ala Lys Tyr Val Ser Leu Asp
                180                 185                 190

Glu Leu Tyr Lys Asn Ser Asp Ala Ile Ile Tyr His Ile Pro Tyr Asn
            195                 200                 205

Lys Glu Thr Glu Asn Met Ile Cys Lys Asp Ser Ile Asn Lys Met Lys
        210                 215                 220

Lys Gly Val Tyr Ile Ile Asn Val Ser Arg Gly Gly Ile Val Asn Asn
225                 230                 235                 240

Lys Asp Leu Leu Asp Gly Leu Lys Ser Gly His Ile Gly Gly Ala Ala
                245                 250                 255
```

```
Leu Asp Val Tyr Thr Asn Glu Ile Glu Tyr Val Asn Lys Asn Ile Lys
            260                 265                 270

Asp Ile Val Leu Lys Asp Glu Ile Ile Glu Glu Leu Phe Lys Met Asp
            275                 280                 285

Asn Val Ile Ile Thr Pro His Phe Ala Phe Tyr Thr Asp Glu Ala Leu
    290                 295                 300

Leu Asn Met Val Ser Ile Ser Ile Asp Asn Ile Phe Glu Phe Lys Asn
305                 310                 315                 320

Thr Gly Lys Cys Val Asn Gln Ile Lys Asn Ile
                325                 330
```

<210> SEQ ID NO 6
<211> LENGTH: 255
<212> TYPE: PRT
<213> ORGANISM: Escherichia coli
<220> FEATURE:
<221> NAME/KEY: MISC_FEATURE
<222> LOCATION: (1)..(255)
<223> OTHER INFORMATION: 7-alpha-Hydroxysteroid Dehydrogenase (HSDH)

<400> SEQUENCE: 6

```
Met Phe Asn Ser Asp Asn Leu Arg Leu Asp Gly Lys Cys Ala Ile Ile
1               5                   10                  15

Thr Gly Ala Gly Ala Gly Ile Gly Lys Glu Ile Ala Ile Thr Phe Ala
            20                  25                  30

Thr Ala Gly Ala Ser Val Val Val Ser Asp Ile Asn Ala Asp Ala Ala
        35                  40                  45

Asn His Val Val Asp Glu Ile Gln Gln Leu Gly Gly Gln Ala Phe Ala
    50                  55                  60

Cys Arg Cys Asp Ile Thr Ser Glu Gln Glu Leu Ser Ala Leu Ala Asp
65                  70                  75                  80

Phe Ala Ile Ser Lys Leu Gly Lys Val Asp Ile Leu Val Asn Asn Ala
                85                  90                  95

Gly Gly Gly Gly Pro Lys Pro Phe Asp Met Pro Met Ala Asp Phe Arg
            100                 105                 110

Arg Ala Tyr Glu Leu Asn Val Phe Ser Phe Phe His Leu Ser Gln Leu
        115                 120                 125

Val Ala Pro Glu Met Glu Lys Asn Gly Gly Gly Val Ile Leu Thr Ile
    130                 135                 140

Thr Ser Met Ala Ala Glu Asn Lys Asn Ile Asn Met Thr Ser Tyr Ala
145                 150                 155                 160

Ser Ser Lys Ala Ala Ala Ser His Leu Val Arg Asn Met Ala Phe Asp
                165                 170                 175

Leu Gly Glu Lys Asn Ile Arg Val Asn Gly Ile Ala Pro Gly Ala Ile
            180                 185                 190

Leu Thr Asp Ala Leu Lys Ser Val Ile Thr Pro Glu Ile Glu Gln Lys
        195                 200                 205

Met Leu Gln His Thr Pro Ile Arg Arg Leu Gly Gln Pro Gln Asp Ile
    210                 215                 220

Ala Asn Ala Ala Leu Phe Leu Cys Ser Pro Ala Ala Ser Trp Val Ser
225                 230                 235                 240

Gly Gln Ile Leu Thr Val Ser Gly Gly Val Gln Glu Leu Asn
                245                 250                 255
```

<210> SEQ ID NO 7
<211> LENGTH: 417

<212> TYPE: PRT
<213> ORGANISM: Sulfobacillus acidophilus DSM 10332
<220> FEATURE:
<221> NAME/KEY: MISC_FEATURE
<222> LOCATION: (1)..(417)
<223> OTHER INFORMATION: Glutamate Dehydrogenase (GDM)

<400> SEQUENCE: 7

```
Met Ala Asp Thr Ser Leu Asn Pro Tyr Val Arg Ala Gln Gln Ser Phe
1               5                   10                  15

Lys Glu Ala Val Glu Thr Leu Gly Leu Glu Pro Ala Val Tyr Glu Ile
            20                  25                  30

Leu Lys Gln Pro Met Arg Thr Phe Glu Val Ala Val Pro Phe Ile Arg
        35                  40                  45

Asp Asp Gly Asn Leu Gln Val Phe Thr Gly Tyr Arg Val Gln His Asn
    50                  55                  60

Asp Ala Leu Gly Pro Thr Lys Gly Gly Leu Arg Phe His Pro Asn Val
65                  70                  75                  80

Asn Leu Asp Glu Val Lys Ala Leu Ala Met Trp Met Thr Val Lys Cys
                85                  90                  95

Ala Leu Leu Glu Leu Pro Tyr Gly Gly Gly Lys Gly Gly Ile Ala Cys
            100                 105                 110

Asp Val Asp Gln Leu Ser Glu Arg Glu Ile Glu Arg Leu Ser Arg Glu
        115                 120                 125

Tyr Ile Arg Ala Ile Asn Leu Val Ile Gly Pro Asp Lys Asp Ile Pro
    130                 135                 140

Ala Pro Asp Val Ser Thr Asn Pro Gln Ile Met Ala Trp Met Val Asp
145                 150                 155                 160

Glu Tyr Ser Arg Ile Arg Gly Glu Asn Thr Phe Gly Leu Ile Thr Gly
                165                 170                 175

Lys Pro Leu Val Ile Gly Gly Ser Arg Gly Arg Val Glu Ala Thr Gly
            180                 185                 190

Arg Gly Leu Val Phe Ala Thr Arg Gln Leu Ala Lys Glu Leu Gly Ile
        195                 200                 205

Glu Phe Glu Lys Ala Arg Val Ala Val Gln Gly Phe Gly Asn Val Gly
    210                 215                 220

Ser Val Ala Ala Ala Ile Ser His Glu Leu Gly Ala Thr Val Val Ala
225                 230                 235                 240

Val Ser Asp Lys Asp Gly Gly Leu Tyr Asn Ala Gly Gly Ile Asn Ile
                245                 250                 255

Pro Asp Leu Leu Glu Tyr Lys Arg Thr His Arg Ala Leu Lys Gly Tyr
            260                 265                 270

Pro Lys Ala Glu Pro Ile Ser Asn Gln Glu Leu Leu Glu Leu Pro Val
        275                 280                 285

Asp Ile Leu Phe Pro Ala Ala Leu Glu Asn Gln Ile Thr Ala Asp Asn
    290                 295                 300

Ala Lys Asn Ile Arg Ala Lys Ile Val Gly Glu Gly Ala Asn Gly Pro
305                 310                 315                 320

Thr Thr Pro Glu Ala Asp Ala Ile Leu Phe Asp Lys Gly Val Met Val
                325                 330                 335

Val Pro Asp Val Leu Gly Asn Ala Gly Gly Val Thr Val Ser Tyr Phe
            340                 345                 350

Glu Trp Val Gln Asn Gln Thr Arg Phe Tyr Trp Ser Glu Glu Glu Val
        355                 360                 365

Asn His Arg Leu Glu Glu Tyr Met Ser Arg Ala Met Ala Glu Met His
```

```
                     370                 375                 380
Arg Met His Glu Arg Tyr Gly Val Thr Leu Arg Lys Ala Ala Tyr Leu
385                 390                 395                 400

Val Ala Thr Glu Arg Val Ala Ser Ala Met Arg Val Arg Gly Trp Leu
                405                 410                 415

Lys

<210> SEQ ID NO 8
<211> LENGTH: 261
<212> TYPE: PRT
<213> ORGANISM: Clostridium sardiniense
<220> FEATURE:
<221> NAME/KEY: MISC_FEATURE
<222> LOCATION: (1)..(261)
<223> OTHER INFORMATION: 7-beta-Hydroxysteroid Dehydrogenase (7b-HSDH)

<400> SEQUENCE: 8

Met Asn Phe Arg Glu Lys Tyr Gly Gln Trp Gly Ile Val Leu Gly Ala
1               5                   10                  15

Thr Glu Gly Ile Gly Lys Ala Ser Ala Phe Glu Leu Ala Lys Arg Gly
                20                  25                  30

Met Asp Val Ile Leu Val Gly Arg Arg Lys Glu Ala Leu Glu Glu Leu
            35                  40                  45

Ala Lys Ala Ile His Glu Glu Thr Gly Lys Glu Ile Arg Val Leu Pro
    50                  55                  60

Gln Asp Leu Ser Glu Tyr Asp Ala Ala Glu Arg Leu Ile Glu Ala Thr
65                  70                  75                  80

Lys Asp Leu Asp Met Gly Val Ile Glu Tyr Val Ala Cys Leu His Ala
                85                  90                  95

Met Gly Gln Tyr Asn Lys Val Asp Tyr Ala Lys Tyr Glu Gln Met Tyr
            100                 105                 110

Arg Val Asn Ile Arg Thr Phe Ser Lys Leu Leu His His Tyr Ile Gly
        115                 120                 125

Glu Phe Lys Glu Arg Asp Arg Gly Ala Phe Ile Thr Ile Gly Ser Leu
130                 135                 140

Ser Gly Trp Thr Ser Leu Pro Phe Cys Ala Glu Tyr Ala Ala Glu Lys
145                 150                 155                 160

Ala Tyr Met Met Thr Val Thr Glu Gly Val Ala Tyr Glu Cys Ala Asn
                165                 170                 175

Thr Asn Val Asp Val Met Leu Leu Ser Ala Gly Ser Thr Ile Thr Pro
            180                 185                 190

Thr Trp Leu Lys Asn Lys Pro Ser Asp Pro Lys Ala Val Ala Ala Ala
        195                 200                 205

Met Tyr Pro Glu Asp Val Ile Lys Asp Gly Phe Glu Gln Leu Gly Lys
    210                 215                 220

Lys Phe Thr Tyr Leu Ala Gly Glu Leu Asn Arg Glu Lys Met Lys Glu
225                 230                 235                 240

Asn Asn Ala Met Asp Arg Asn Asp Leu Ile Ala Lys Leu Gly Lys Met
                245                 250                 255

Phe Asp His Met Ala
            260

<210> SEQ ID NO 9
<211> LENGTH: 244
<212> TYPE: PRT
<213> ORGANISM: Agromyces mediolanus
<220> FEATURE:
```

```
<221> NAME/KEY: MISC_FEATURE
<222> LOCATION: (1)..(244)
<223> OTHER INFORMATION: Halohydrin Dehalogenase (HheA)

<400> SEQUENCE: 9

Met Arg Ile Ala Leu Val Thr His Ala Arg His Phe Ala Gly Pro Ala
1               5                   10                  15

Ala Val Glu Ala Leu Thr Arg Asp Gly Tyr Thr Val Val Cys His Asp
            20                  25                  30

Ala Ser Phe Ala Asp Ala Ala Glu Arg Gln Arg Phe Glu Ser Glu Asn
        35                  40                  45

Pro Gly Thr Ile Ala Leu Ala Glu Gln Lys Pro Glu Arg Leu Val Asp
    50                  55                  60

Ala Thr Leu Gln Tyr Gly Glu Ala Ile Asp Thr Ile Val Ser Asn Asp
65                  70                  75                  80

Tyr Ile Pro Arg Pro Met Asn Arg Leu Pro Ile Glu Gly Thr Ser Glu
                85                  90                  95

Ala Asp Ile Arg Gln Met Phe Glu Ala Leu Ser Ile Phe Pro Ile Leu
            100                 105                 110

Leu Leu Gln Ser Ala Ile Ala Pro Leu Arg Ala Ala Gly Gly Ala Ser
        115                 120                 125

Val Ile Phe Ile Thr Ser Ser Val Gly Lys Lys Pro Leu Ala Tyr Asn
    130                 135                 140

Pro Leu Tyr Gly Pro Ala Arg Ala Ala Thr Val Ala Leu Val Glu Ser
145                 150                 155                 160

Ala Ala Lys Thr Leu Ser Arg Asp Gly Ile Leu Leu Tyr Ala Ile Gly
                165                 170                 175

Pro Asn Phe Phe Asn Asn Pro Thr Tyr Phe Pro Thr Ser Asp Trp Glu
            180                 185                 190

Asn Asp Pro Glu Leu Arg Asp Arg Val Glu Arg Asp Val Pro Leu Gly
        195                 200                 205

Arg Leu Gly Arg Pro Asp Glu Met Gly Ala Leu Ile Thr Phe Leu Ala
    210                 215                 220

Ser Arg Arg Ala Ala Pro Ile Val Gly Gln Phe Phe Ala Phe Thr Gly
225                 230                 235                 240

Gly Tyr Leu Pro

<210> SEQ ID NO 10
<211> LENGTH: 796
<212> TYPE: PRT
<213> ORGANISM: Escherichia coli PCN009
<220> FEATURE:
<221> NAME/KEY: MISC_FEATURE
<222> LOCATION: (1)..(796)
<223> OTHER INFORMATION: Glucose Dehydrogenase (GDH)

<400> SEQUENCE: 10

Met Ala Ile Asn Asn Thr Gly Ser Arg Arg Leu Leu Val Thr Leu Thr
1               5                   10                  15

Ala Leu Phe Ala Ala Leu Cys Gly Leu Tyr Leu Leu Ile Gly Gly Gly
            20                  25                  30

Trp Leu Val Ala Ile Gly Gly Ser Trp Tyr Tyr Pro Ile Ala Gly Leu
        35                  40                  45

Val Met Leu Gly Val Ala Trp Met Leu Trp Arg Ser Lys Arg Ala Ala
    50                  55                  60

Leu Trp Leu Tyr Ala Ala Leu Leu Leu Gly Thr Met Ile Trp Gly Val
65                  70                  75                  80
```

```
Trp Glu Val Gly Phe Asp Phe Trp Ala Leu Thr Pro Arg Ser Asp Ile
                85                  90                  95

Leu Val Phe Phe Gly Ile Trp Leu Ile Leu Pro Phe Val Trp Arg Arg
            100                 105                 110

Leu Val Ile Pro Ala Ser Gly Ala Val Ala Ala Leu Val Ala Leu
        115                 120                 125

Leu Ile Ser Gly Ser Ile Leu Thr Trp Ala Gly Phe Asn Asp Pro Gln
        130                 135                 140

Glu Ile Asn Gly Thr Leu Ser Ala Asp Ala Thr Pro Ala Glu Ala Ile
145                 150                 155                 160

Ser Pro Val Ala Asp Gln Asp Trp Pro Ala Tyr Gly Arg Asn Gln Glu
                165                 170                 175

Gly Gln Arg Phe Ser Pro Leu Lys Gln Ile Asn Ala Asp Asn Val His
            180                 185                 190

Asn Leu Lys Glu Ala Trp Val Phe Arg Thr Gly Asp Val Lys Gln Pro
        195                 200                 205

Asn Asp Pro Gly Glu Ile Thr Asn Glu Val Thr Pro Ile Lys Val Gly
        210                 215                 220

Asp Thr Leu Tyr Leu Cys Thr His Gln Arg Leu Phe Ala Leu Asp
225                 230                 235                 240

Ala Ala Ser Gly Lys Glu Lys Trp His Tyr Asp Pro Glu Leu Lys Thr
                245                 250                 255

Asn Glu Ser Phe Gln His Val Thr Cys Arg Gly Val Ser Tyr His Glu
            260                 265                 270

Ala Lys Ala Glu Thr Ala Ser Pro Glu Val Met Ala Asp Cys Pro Arg
        275                 280                 285

Arg Ile Ile Leu Pro Val Asn Asp Gly Arg Leu Ile Ala Ile Asn Ala
        290                 295                 300

Glu Asn Gly Lys Leu Cys Glu Thr Phe Ala Asn Lys Gly Val Leu Asn
305                 310                 315                 320

Leu Gln Ser Asn Met Pro Asp Thr Lys Pro Gly Leu Tyr Glu Pro Thr
                325                 330                 335

Ser Pro Pro Ile Ile Thr Asp Lys Thr Ile Val Met Ala Gly Ser Val
            340                 345                 350

Thr Asp Asn Phe Ser Thr Arg Glu Thr Ser Gly Val Ile Arg Gly Phe
        355                 360                 365

Asp Val Asn Thr Gly Glu Leu Leu Trp Ala Phe Asp Pro Gly Ala Lys
370                 375                 380

Asp Pro Asn Ala Ile Pro Ser Asp Glu His Thr Phe Thr Phe Asn Ser
385                 390                 395                 400

Pro Asn Ser Trp Ala Pro Ala Tyr Asp Ala Lys Leu Asp Leu Val
                405                 410                 415

Tyr Leu Pro Met Gly Val Thr Thr Pro Asp Ile Trp Gly Gly Asn Arg
            420                 425                 430

Thr Pro Glu Gln Glu Arg Tyr Ala Ser Ser Ile Leu Ala Leu Asn Ala
        435                 440                 445

Thr Thr Gly Lys Leu Ala Trp Ser Tyr Gln Thr Val His His Asp Leu
450                 455                 460

Trp Asp Met Asp Leu Pro Ala Gln Pro Thr Leu Ala Asp Ile Thr Val
465                 470                 475                 480

Asn Gly Gln Lys Val Pro Val Ile Tyr Ala Pro Ala Lys Thr Gly Asn
                485                 490                 495
```

```
Ile Phe Val Leu Asp Arg Arg Asn Gly Glu Leu Val Val Pro Ala Pro
            500                 505                 510

Glu Lys Pro Val Pro Gln Gly Ala Ala Lys Gly Asp Tyr Val Thr Pro
        515                 520                 525

Thr Gln Pro Phe Ser Glu Leu Ser Phe Arg Pro Thr Lys Asp Leu Ser
    530                 535                 540

Gly Ala Asp Met Trp Gly Ala Thr Met Phe Asp Gln Leu Val Cys Arg
545                 550                 555                 560

Val Met Phe His Gln Met Arg Tyr Glu Gly Ile Phe Thr Pro Pro Ser
                565                 570                 575

Glu Gln Gly Thr Leu Val Phe Pro Gly Asn Leu Gly Met Phe Glu Trp
            580                 585                 590

Gly Gly Ile Ser Val Asp Pro Asn Arg Glu Val Ala Ile Ala Asn Pro
        595                 600                 605

Met Ala Leu Pro Phe Val Ser Lys Leu Ile Pro Arg Gly Pro Gly Asn
    610                 615                 620

Pro Met Glu Gln Pro Lys Asp Ala Lys Gly Thr Gly Thr Glu Ser Gly
625                 630                 635                 640

Ile Gln Pro Gln Tyr Gly Val Pro Tyr Gly Val Thr Leu Asn Pro Phe
                645                 650                 655

Leu Ser Pro Phe Gly Leu Pro Cys Lys Gln Pro Ala Trp Gly Tyr Ile
            660                 665                 670

Ser Ala Leu Asp Leu Lys Thr Asn Glu Val Val Trp Lys Lys Arg Ile
        675                 680                 685

Gly Thr Pro Gln Asp Ser Met Pro Phe Pro Met Pro Val Pro Val Pro
    690                 695                 700

Phe Asn Met Gly Met Pro Met Leu Gly Gly Pro Ile Ser Thr Ala Gly
705                 710                 715                 720

Asn Val Leu Phe Ile Ala Ala Thr Ala Asp Asn Tyr Leu Arg Ala Tyr
                725                 730                 735

Asn Met Ser Asn Gly Glu Lys Leu Trp Gln Gly Arg Leu Pro Ala Gly
            740                 745                 750

Gly Gln Ala Thr Pro Met Thr Tyr Glu Val Asn Gly Lys Gln Tyr Val
        755                 760                 765

Val Ile Ser Ala Gly Gly His Gly Ser Phe Gly Thr Lys Met Gly Asp
    770                 775                 780

Tyr Ile Val Ala Tyr Ala Leu Pro Asp Asp Val Lys
785                 790                 795

<210> SEQ ID NO 11
<211> LENGTH: 294
<212> TYPE: PRT
<213> ORGANISM: Lactobacillus
<220> FEATURE:
<221> NAME/KEY: MISC_FEATURE
<222> LOCATION: (1)..(294)
<223> OTHER INFORMATION: Ketoreductase
<220> FEATURE:
<221> NAME/KEY: MISC_FEATURE
<222> LOCATION: (1)..(294)
<223> OTHER INFORMATION: Originating from Lactobacillus silage

<400> SEQUENCE: 11

Met Ser Lys Ile Ile Leu Ile Thr Gly Ala Thr Asp Gly Ile Gly Lys
1               5                   10                  15

Ala Thr Ala Met Ala Leu Ala Gln Ala Gly His His Val Ile Ile His
            20                  25                  30
```

```
Gly Arg Asn Glu Glu Lys Ala Lys Arg Ile Val Gln Glu Ile Val Thr
            35                  40                  45

Lys Thr Asn Asn Thr Gln Val Asp Tyr Leu Ile Ala Asp Leu Phe Ser
 50                  55                  60

Met Ala Ala Ile Lys Arg Met Val Asn Glu Phe Asn Gln Arg Tyr Ala
 65                  70                  75                  80

His Leu Asp Val Leu Ile Asn Asn Ala Gly Ala Val Phe Asn Asn Glu
                 85                  90                  95

Arg Ala Glu Ser Ala Asp Gly Ile Glu Lys Thr Met Ala Leu Asn Val
            100                 105                 110

Ile Ala Pro Phe Leu Leu Asn Gln Leu Leu Ser Ser Leu Thr Lys
            115                 120                 125

Ser Ser Asp Gly Arg Ile Ile Asn Thr Ser Ser Ala Ser His Arg Ala
130                 135                 140

Ser Gly Arg Pro Asp Met Thr Asp Leu Asn Leu Lys Lys Thr Tyr Ser
145                 150                 155                 160

Ala Gln Arg Arg Tyr Ser Leu Ala Lys Leu Phe Val Ile Trp Asn Thr
                165                 170                 175

Gln His Gln Ala Ala Glu Leu Gln Gln Lys Gly Ile Lys Asn Val Thr
            180                 185                 190

Val Asn Ala Ser His Pro Gly Ala Val Ala Thr Asn Phe Gly Gln Asp
            195                 200                 205

Ser Asp Lys Gly Leu Leu Val Asn Leu Ile Tyr Lys Ile Ala Ile Gln
            210                 215                 220

Leu Ser Lys Phe Glu Pro Phe Lys Leu Met Ala Ser Pro Glu Lys Gly
225                 230                 235                 240

Ala Ser Thr Asn Val Tyr Leu Ala Val Ser Ser Ala Val Arg Gly Ile
                245                 250                 255

Thr Gly Gln Tyr Trp Gly Asn Ser Lys Ala Leu Lys Pro Asp Thr Arg
            260                 265                 270

Tyr Cys Ser Arg Ala Asn Glu Gln Arg Leu Trp Asp Tyr Cys Met Thr
            275                 280                 285

Thr Val Lys Pro Tyr Leu
            290

<210> SEQ ID NO 12
<211> LENGTH: 549
<212> TYPE: PRT
<213> ORGANISM: Pseudomonas veronii 1YdBTEX2
<220> FEATURE:
<221> NAME/KEY: MISC_FEATURE
<222> LOCATION: (1)..(549)
<223> OTHER INFORMATION: Baeyer-Villiger Monooxygenase (BVMO)

<400> SEQUENCE: 12

Met Ser Ala Gln Ser Lys Leu Ala Ala Val Ser Ala Glu Asn Gly Lys
1               5                   10                  15

Val Thr Tyr Leu Asp Ala Met Val Ile Gly Ala Gly Val Ala Gly Leu
            20                  25                  30

Tyr Gln Leu Tyr Arg Leu Arg Glu Met Gly Leu Thr Val Arg Ala Tyr
            35                  40                  45

Asp Thr Ala Ser Gly Val Gly Gly Thr Trp Tyr Trp Asn Arg Tyr Pro
 50                  55                  60

Gly Ala Arg Phe Asp Ser Gln Ala Glu Ile Tyr Gln Tyr Trp Phe Ser
 65                  70                  75                  80

Glu Glu Leu Tyr Lys Ser Trp Gln Pro Thr Glu Arg Phe Pro Ala Gln
```

```
                85                 90                 95
Pro Glu Thr Glu Gln Trp Leu Asn Phe Val Ala Asn Arg Leu Asp Leu
                100                105                110
Lys Lys Asp Ile Gln Phe Asn Thr Arg Ile Ala Ala Tyr Phe Cys
        115                120                125
Glu Glu Ser Gly Tyr Trp Arg Val Thr Thr Glu Ala Gly Glu Thr Ile
130                135                140
Asn Thr Gln Tyr Leu Ile Ser Cys Cys Gly Met Leu Ser Ala Pro Leu
145                150                155                160
Ser Asp Arg Phe Pro Gly Gln Thr Asp Phe Asn Gly Gln Ile Tyr His
                165                170                175
Thr Gly Leu Trp Pro Lys Asp Pro Val Asp Phe Ser Gly Lys Arg Val
                180                185                190
Ala Val Val Gly Thr Gly Ala Thr Gly Ile Gln Val Ile Gln Thr Ile
                195                200                205
Ala Pro Ala Val Gly Ser Met Lys Val Phe Val Arg Thr Pro Gln Tyr
210                215                220
Val Ile Pro Met Arg Asn Pro Lys Tyr Ser Lys Glu Asp Trp Glu Lys
225                230                235                240
Trp Gly Thr Gln Phe His Gln Leu Lys Lys Arg Val Arg Glu Thr Phe
                245                250                255
Ala Gly Phe Asp Tyr Asp Phe Asp Ala Gly Pro Trp Ala Glu Lys Thr
                260                265                270
Pro Asp Glu Arg Gln Ala Val Leu Glu Gln Leu Trp Glu Asp Gly Ser
        275                280                285
Leu Ala Met Trp Leu Ala Ser Phe Pro Glu Met Phe Phe Asp Glu Gln
290                295                300
Val Asn Glu Val Val Ser Glu Phe Val Arg Ile Lys Met Arg Glu Arg
305                310                315                320
Leu Gln Ser Arg Pro Asp Leu Cys Asn Leu Leu Ile Pro Thr Asp Tyr
                325                330                335
Gly Phe Gly Thr His Arg Val Pro Leu Glu Ser Lys Tyr Leu Glu Val
                340                345                350
Tyr Leu Gln Pro Asn Val Glu Ala Val Asp Cys Lys Gln Ser Pro Ile
        355                360                365
Glu Arg Ile Val Pro Glu Gly Ile Gln Thr Ala Asp Gly Lys Ile His
        370                375                380
Glu Val Asp Ile Ile Val Leu Ala Val Gly Phe Asp Ala Gly Ser Gly
385                390                395                400
Ala Leu Ser Arg Ile Asp Ile Arg Gly Arg Asp Asn Arg Ser Leu Arg
                405                410                415
Glu Gln Trp Lys Gln Glu Ile Arg Thr Ser Met Gly Leu Gln Ile His
                420                425                430
Gly Tyr Pro Asn Leu Phe Thr Thr Gly Ala Pro Leu Ala Pro Ser Ala
                435                440                445
Ala Leu Cys Asn Met Thr Thr Cys Leu Gln Gln Val Asp Trp Ile
        450                455                460
Thr Gly Cys Ile Glu Phe Ala Ile Gln His Gly Lys Gln Val Val Glu
465                470                475                480
Ala Ser Lys Glu Phe Glu Asp Asp Trp Val Gln His Asp Glu Thr
        485                490                495
Ala Ala Lys Thr Leu Val Val Lys Thr Asp Ser Trp Tyr Met Gly Ser
        500                505                510
```

```
Asn Val Asp Gly Lys Pro Arg Arg Leu Val Ser Tyr Ile Gly Gly Val
        515                 520                 525

Gly Asn Tyr His Arg Arg Cys Asp Glu Ile Ala Ala Gln Gly Tyr Pro
        530                 535                 540

Gly Phe Glu Met Ala
545

<210> SEQ ID NO 13
<211> LENGTH: 366
<212> TYPE: PRT
<213> ORGANISM: Sulfobacillus acidophilus DSM 10332
<220> FEATURE:
<221> NAME/KEY: MISC_FEATURE
<222> LOCATION: (1)..(366)
<223> OTHER INFORMATION: Alanine Dehydrogenase (AlaDH)

<400> SEQUENCE: 13

Met Lys Ile Gly Val Pro Lys Glu Ile Lys Thr Tyr Glu Asn Arg Val
1               5                   10                  15

Ala Leu Thr Pro Ser Gly Val Ala Ala Leu Thr Gln Ala Gly His Gln
            20                  25                  30

Val Leu Val Glu Thr Ser Ala Gly Ser Ala Cys Gly Tyr Pro Asp Glu
        35                  40                  45

Gln Tyr Arg Arg Ala Gly Ala Gln Met Thr Thr Ala Ala Glu Ala Trp
    50                  55                  60

Ser Ala Asp Leu Val Val Lys Val Lys Glu Pro Gln Pro Val Glu Tyr
65                  70                  75                  80

Gly Tyr Phe Arg Pro Asn Leu Met Leu Phe Thr Tyr Leu His Leu Ala
                85                  90                  95

Ala Ala Pro Asp Leu Ala Asp Ala Leu Met Ala Glu Gly Val Thr Ala
            100                 105                 110

Ile Gly Tyr Glu Thr Val Gln Asp Ala Glu Gly Arg Leu Pro Leu Leu
        115                 120                 125

Ala Pro Met Ser Glu Ile Ala Gly Arg Leu Ala Pro Gln Leu Gly Ala
    130                 135                 140

Gln Tyr Leu Glu Asn His Gln Gly Gly Leu Gly Ile Leu Ile Ser Gly
145                 150                 155                 160

Val Pro Gly Val Pro Ala Ala His Val Val Ile Val Gly Gly Gly Thr
                165                 170                 175

Val Gly Thr Ala Ala Ala Lys Met Ala Val Gly Met Gly Ala Arg Val
            180                 185                 190

Ser Ile Leu Asp Ile Asn Pro Asn Arg Leu Ala Trp Leu Asp Asp Val
        195                 200                 205

Phe Gly Ser Arg Ile Gln Thr Leu Trp Ala His Pro Ala Ala Leu Gly
    210                 215                 220

Asp Ala Val Arg Ser Ala Asp Ile Val Ile Gly Ala Val Leu Val Pro
225                 230                 235                 240

Gly Asp Arg Ala Pro Lys Val Val Thr Thr Glu Met Val Gln Gln Met
                245                 250                 255

Thr Ala Gly Ser Val Ile Val Asp Val Ala Ile Asp Gln Gly Gly Cys
            260                 265                 270

Val Glu Thr Ile Asp Arg Ala Thr Thr His Glu Asn Pro Thr Tyr Thr
        275                 280                 285

Arg Phe Gly Val Thr His Tyr Ala Val Ala Asn Ile Pro Gly Ser Val
    290                 295                 300
```

```
Ala Arg Thr Ala Thr Gln Ala Leu Thr Asn Val Thr Leu Pro Tyr Val
305                 310                 315                 320

Ile Ala Leu Ser Arg Gly Leu Thr Gly Ala Leu Gln Glu Arg Pro Glu
            325                 330                 335

Leu Arg Ser Gly Ile Asn Ile Ala Asp Gly Arg Ile Thr His Ala Ala
        340                 345                 350

Val Ala Lys Ala Leu Asp Arg Ala Tyr His Pro Leu Thr Leu
    355                 360                 365

<210> SEQ ID NO 14
<211> LENGTH: 355
<212> TYPE: PRT
<213> ORGANISM: Sulfobacillus acidophilus DSM 10332
<220> FEATURE:
<221> NAME/KEY: MISC_FEATURE
<222> LOCATION: (1)..(355)
<223> OTHER INFORMATION: Phenylalanine Dehydrogenase (PheDH)

<400> SEQUENCE: 14

Met Glu Ile Phe Glu Glu Ile Lys Arg Arg Gly His Glu Gln Ile Leu
1               5                   10                  15

Phe Asn Tyr Asp Arg Ala Ser Gly Leu Lys Ala Ile Ile Ala Ile His
            20                  25                  30

Asn Thr Thr Leu Gly Pro Ala Leu Gly Gly Cys Arg Met Leu Pro Tyr
        35                  40                  45

Gln Thr Glu Glu Ala Ala Leu Glu Asp Ala Leu Arg Leu Ser Glu Gly
    50                  55                  60

Met Thr Tyr Lys Ala Ala Ala Gly Leu Asp Phe Gly Gly Gly Lys
65                  70                  75                  80

Thr Val Ile Ile Gly Asp Pro Met Lys Asp Lys Ser Glu Ala Leu Phe
                85                  90                  95

Arg Ala Leu Gly Arg Phe Ile Glu Thr Leu Lys Gly Arg Tyr Leu Thr
            100                 105                 110

Gly Glu Asp Val Gly Thr Asn Glu Glu Asp Phe Val Trp Ala Arg Arg
        115                 120                 125

Glu Thr Arg Tyr Val Val Gly Leu Pro Pro Ala Tyr Gly Gly Ser Gly
    130                 135                 140

Asp Thr Gly Asp Asn Thr Ala Arg Gly Val Ile Gln Ala Met Arg Ala
145                 150                 155                 160

Ala Leu Met His Arg Tyr Gly Ser Pro Asp Leu Gln Gly Arg Arg Ile
                165                 170                 175

Ala Val Gln Gly Leu Gly Lys Val Gly Tyr His Val Ala Arg Arg Ala
            180                 185                 190

Ile Glu Ala Gly Ala Arg Val Ile Ala Ala Asp Ile Asn Pro His Val
        195                 200                 205

Val Gly Arg Val Ala Ser Ala Trp Gly Ile Glu Ala Thr Asp Pro Trp
    210                 215                 220

Ala Val Val Glu Thr Pro Cys Asp Ile Phe Ala Pro Cys Ala Leu Gly
225                 230                 235                 240

Asn Val Ile Thr Glu Arg Thr Val Ser Ala Leu Gln Cys Gln Val Val
                245                 250                 255

Ala Gly Ser Ala Asn Asn Gln Leu Ala Asp Asp Arg Leu Ala Asp Asp
            260                 265                 270

Leu Ala Ala Arg Gly Ile Leu Tyr Ala Pro Asp Phe Ile Ala Asn Ala
        275                 280                 285

Gly Gly Leu Ile Gln Val Ala Asp Glu Ile Arg Gly Tyr His Glu Glu
```

```
                290                 295                 300
Arg Val Arg His Gln Ile Asp Gly Ile Tyr Asp Val Leu Leu Glu Ile
305                 310                 315                 320

Phe Arg Lys Ala Asp Ala Ser Gly Arg Ser Thr Val Ala Val Ala Val
                325                 330                 335

Asp Glu Ala Arg Arg Leu Asp Thr Ile Gln Ala Ile His Arg Leu
                340                 345                 350

Tyr Gly Ser
        355

<210> SEQ ID NO 15
<211> LENGTH: 358
<212> TYPE: PRT
<213> ORGANISM: Sulfobacillus acidophilus DSM 10332
<220> FEATURE:
<221> NAME/KEY: MISC_FEATURE
<222> LOCATION: (1)..(358)
<223> OTHER INFORMATION: Leucine Dehydrogenase (LeuDH)

<400> SEQUENCE: 15

Met Asn Ile Phe Glu Gln Met Glu Lys Tyr Gly His Glu Gln Val Val
1               5                   10                  15

Phe Trp Tyr Asp Lys Thr Thr Gly Leu Lys Ala Ile Val Gly Ile His
                20                  25                  30

Asp Thr Thr Leu Gly Pro Ala Leu Gly Gly Cys Arg Met Trp Pro Tyr
            35                  40                  45

Ala Ser Glu Glu Asp Ala Ile Thr Asp Val Leu Arg Leu Ser Arg Gly
        50                  55                  60

Met Thr Tyr Lys Asn Ala Ala Met Gly Leu Asp Leu Gly Gly Gly Lys
65                  70                  75                  80

Ser Val Ile Trp Ala Asp Ser Arg Thr Asp Lys Ser Glu Ala Leu Phe
                85                  90                  95

Arg Ser Phe Gly Arg Leu Ile Gln Ser Leu Gly Gly Arg Tyr Ile Thr
            100                 105                 110

Ala Glu Asp Val Gly Thr Asn Ala Asp Asp Met Ala Val Val Ala Arg
        115                 120                 125

Glu Thr Ala Phe Val Gly Gly Leu Lys Glu Thr Ser Gly Asp Pro Ser
130                 135                 140

Pro Ala Thr Ala Leu Gly Val Leu Glu Gly Met Lys Ala Ala Ala Asn
145                 150                 155                 160

Met Val Trp Gly Ser Glu Ser Leu Arg Gly Lys His Val Ala Ile Gln
                165                 170                 175

Gly Leu Gly His Val Gly Ser Ile Leu Ala Arg Met Leu Leu Asp Glu
            180                 185                 190

Gly Ala Gln Leu Thr Val Thr Asp Ile His Val Glu Gly Ala Arg Pro
        195                 200                 205

Leu Ala Glu Ser Leu Gly Val Ala Trp Val Asp Pro Glu Ala Ile Tyr
210                 215                 220

Asp Val Ala Cys Asp Ile Phe Ala Pro Cys Ala Leu Gly Ala Ile Leu
225                 230                 235                 240

Asn Asp Glu Thr Ile Pro Arg Leu Gln Cys Lys Ile Val Ala Gly Ser
                245                 250                 255

Ala Asn Asn Gln Leu Lys Glu Pro Arg His Gly Leu Glu Leu Met Arg
            260                 265                 270

Arg Asn Ile Leu Tyr Val Pro Asp Tyr Val Ile Asn Gly Gly Gly Val
        275                 280                 285
```

Val Asn Val Ala Asp Glu Phe His Arg Asp Gly Tyr His Arg Glu Arg
        290                 295                 300

Ala Tyr Ala Arg Val Arg Gln Ile Gly Gln Gln Val Ser Gln Ile Leu
305                 310                 315                 320

Ala His Ala Glu Glu Thr Asn Val Pro Thr Gln Glu Ala Ala Asp Gln
                325                 330                 335

Val Ala Glu Gln Arg Ile Arg Thr Leu Gly Lys Val Lys Ser Gly Phe
        340                 345                 350

Leu Pro Pro Ala Arg Arg
        355

<210> SEQ ID NO 16
<211> LENGTH: 424
<212> TYPE: PRT
<213> ORGANISM: Drosophila melanogaster
<220> FEATURE:
<221> NAME/KEY: MISC_FEATURE
<222> LOCATION: (1)..(424)
<223> OTHER INFORMATION: Glutamate Oxaloacetate Transaminase (GOT)

<400> SEQUENCE: 16

Met Ser Gln Ile Cys Lys Arg Gly Leu Leu Ile Ser Asn Arg Leu Ala
1               5                   10                  15

Pro Ala Leu Arg Cys Lys Ser Thr Trp Phe Ser Glu Val Gln Met
            20                  25                  30

Gly Pro Pro Asp Ala Ile Leu Gly Val Thr Glu Ala Phe Lys Lys Asp
        35                  40                  45

Thr Asn Pro Lys Lys Ile Asn Leu Gly Ala Gly Ala Tyr Arg Asp Asp
50                  55                  60

Asn Thr Gln Pro Phe Val Leu Pro Ser Val Arg Glu Ala Glu Lys Arg
65                  70                  75                  80

Val Val Ser Arg Ser Leu Asp Lys Glu Tyr Ala Thr Ile Ile Gly Ile
                85                  90                  95

Pro Glu Phe Tyr Asn Lys Ala Ile Glu Leu Ala Leu Gly Lys Gly Ser
            100                 105                 110

Lys Arg Leu Ala Ala Lys His Asn Val Thr Ala Gln Ser Ile Ser Gly
        115                 120                 125

Thr Gly Ala Leu Arg Ile Gly Ala Ala Phe Leu Ala Lys Phe Trp Gln
130                 135                 140

Gly Asn Arg Glu Ile Tyr Ile Pro Ser Pro Ser Trp Gly Asn His Val
145                 150                 155                 160

Ala Ile Phe Glu His Ala Gly Leu Pro Val Asn Arg Tyr Arg Tyr Tyr
                165                 170                 175

Asp Lys Asp Thr Cys Ala Leu Asp Phe Gly Gly Leu Ile Glu Asp Leu
            180                 185                 190

Lys Lys Ile Pro Glu Lys Ser Ile Val Leu Leu His Ala Cys Ala His
        195                 200                 205

Asn Pro Thr Gly Val Asp Pro Thr Leu Glu Gln Trp Arg Glu Ile Ser
210                 215                 220

Ala Leu Val Lys Lys Arg Asn Leu Tyr Pro Phe Ile Asp Met Ala Tyr
225                 230                 235                 240

Gln Gly Phe Ala Thr Gly Asp Ile Asp Arg Asp Ala Gln Ala Val Arg
                245                 250                 255

Thr Phe Glu Ala Asp Gly His Asp Phe Cys Leu Ala Gln Ser Phe Ala
            260                 265                 270

```
Lys Asn Met Gly Leu Tyr Gly Glu Arg Ala Gly Ala Phe Thr Val Leu
                275                 280                 285

Cys Ser Asp Glu Glu Ala Ala Arg Val Met Ser Gln Val Lys Ile
    290                 295                 300

Leu Ile Arg Gly Leu Tyr Ser Asn Pro Val His Gly Ala Arg Ile
305                 310                 315                 320

Ala Ala Glu Ile Leu Asn Asn Glu Asp Leu Arg Ala Gln Trp Leu Lys
                325                 330                 335

Asp Val Lys Leu Met Ala Asp Arg Ile Ile Asp Val Arg Thr Lys Leu
                340                 345                 350

Lys Asp Asn Leu Ile Lys Leu Gly Ser Ser Gln Asn Trp Asp His Ile
                355                 360                 365

Val Asn Gln Ile Gly Met Phe Cys Phe Thr Gly Leu Lys Pro Glu Gln
370                 375                 380

Val Gln Lys Leu Ile Lys Asp His Ser Val Tyr Leu Thr Asn Asp Gly
385                 390                 395                 400

Arg Val Ser Met Ala Gly Val Thr Ser Lys Asn Val Glu Tyr Leu Ala
                405                 410                 415

Glu Ser Ile His Lys Val Thr Lys
                420

<210> SEQ ID NO 17
<211> LENGTH: 398
<212> TYPE: PRT
<213> ORGANISM: Bacillus subtilis
<220> FEATURE:
<221> NAME/KEY: MISC_FEATURE
<222> LOCATION: (1)..(398)
<223> OTHER INFORMATION: Transaminase (TA)

<400> SEQUENCE: 17

Met Lys Phe Glu Gln Ser His Val Leu Lys Glu Leu Pro Lys Gln Phe
1               5                   10                  15

Phe Ala Ser Leu Val Gln Lys Val Asn Arg Lys Leu Ala Glu Gly His
                20                  25                  30

Asp Val Ile Asn Leu Gly Gln Gly Asn Pro Asp Gln Pro Thr Pro Glu
            35                  40                  45

His Ile Val Glu Glu Met Lys Arg Ala Val Ala Asp Pro Glu Asn His
        50                  55                  60

Lys Tyr Ser Ser Phe Arg Gly Ser Tyr Arg Leu Lys Ser Ala Ala Ala
65                  70                  75                  80

Ala Phe Tyr Lys Arg Glu Tyr Gly Ile Asp Leu Asp Pro Glu Thr Glu
                85                  90                  95

Val Ala Val Leu Phe Gly Gly Lys Ala Gly Leu Val Glu Leu Pro Gln
            100                 105                 110

Cys Leu Leu Asn Pro Gly Asp Thr Ile Leu Val Pro Asp Pro Gly Tyr
        115                 120                 125

Pro Asp Tyr Trp Ser Gly Val Thr Leu Ala Lys Ala Lys Met Glu Met
    130                 135                 140

Met Pro Leu Val Lys Asp Arg Ala Phe Leu Pro Asp Tyr Ser Ser Ile
145                 150                 155                 160

Thr Ala Glu Ile Arg Glu Gln Ala Lys Leu Met Tyr Leu Asn Tyr Pro
                165                 170                 175

Asn Asn Pro Thr Gly Ala Val Ala Thr Ser Glu Phe Phe Glu Asp Thr
            180                 185                 190

Val Arg Phe Ala Ala Glu Asn Gly Ile Cys Val Val His Asp Phe Ala
```

```
            195                 200                 205
Tyr Gly Ala Val Gly Phe Asp Gly Cys Lys Pro Leu Ser Phe Leu Gln
210                 215                 220

Thr Glu Gly Ala Lys Asp Ile Gly Ile Glu Ile Tyr Thr Leu Ser Lys
225                 230                 235                 240

Thr Tyr Asn Met Ala Gly Trp Arg Val Gly Phe Ala Val Gly Asn Ala
                245                 250                 255

Ser Val Ile Glu Ala Ile Asn Leu Tyr Gln Asp His Met Phe Val Ser
                260                 265                 270

Leu Phe Arg Ala Thr Gln Glu Ala Ala Glu Ala Leu Leu Ala Asp
                275                 280                 285

Gln Thr Cys Val Ala Glu Gln Asn Ala Arg Tyr Glu Ser Arg Arg Asn
290                 295                 300

Ala Trp Ile Thr Ala Cys Arg Glu Ile Gly Trp Asp Val Thr Ala Pro
305                 310                 315                 320

Ala Gly Ser Phe Phe Ala Trp Leu Pro Val Pro Glu Gly Tyr Thr Ser
                325                 330                 335

Glu Gln Phe Ser Asp Leu Leu Leu Glu Lys Ala Asn Val Ala Val Ala
                340                 345                 350

Ala Gly Asn Gly Phe Gly Glu Tyr Gly Glu Gly Tyr Val Arg Val Gly
                355                 360                 365

Leu Leu Thr Ser Glu Glu Arg Leu Lys Glu Ala Ala Tyr Arg Ile Gly
                370                 375                 380

Lys Leu Asn Leu Phe Thr Gln Lys Ser Ile Asp Lys Thr Leu
385                 390                 395

<210> SEQ ID NO 18
<211> LENGTH: 470
<212> TYPE: PRT
<213> ORGANISM: Plasmodium falciparum
<220> FEATURE:
<221> NAME/KEY: MISC_FEATURE
<222> LOCATION: (1)..(470)
<223> OTHER INFORMATION: Glutamate Dehydrogenase (GluDH)

<400> SEQUENCE: 18

Met Ser Ala Leu Lys Asp Lys Thr Gly Arg Phe Val Val Leu Asp Lys
1               5                   10                  15

Asn Ala Ser Asn Tyr Glu Ser Leu Val Asp Gln Glu Met Asn Asn Val
                20                  25                  30

Tyr Glu Arg Val Met Lys Leu Asp Pro Asn Gln Val Glu Phe Leu Gln
                35                  40                  45

Ala Phe His Glu Ile Leu Tyr Ser Leu Lys Pro Leu Phe Met Glu Glu
                50                  55                  60

Pro Lys Tyr Leu Pro Ile Ile Glu Thr Leu Ser Glu Pro Glu Arg Ala
65                  70                  75                  80

Ile Gln Phe Arg Val Cys Trp Leu Asp Asp Asn Gly Val Gln Arg Lys
                85                  90                  95

Asn Arg Cys Phe Arg Val Gln Tyr Asn Ser Ala Leu Gly Pro Tyr Lys
                100                 105                 110
```

-continued

```
Gly Gly Leu Arg Phe His Pro Ser Val Asn Leu Ser Ile Val Lys Phe
            115                 120                 125

Leu Gly Phe Glu Gln Ile Phe Lys Asn Ser Leu Thr Gly Leu Ser Met
130                 135                 140

Gly Gly Gly Lys Gly Gly Ser Asp Phe Asp Pro Lys Gly Lys Ser Asp
145                 150                 155                 160

Asn Glu Ile Leu Lys Phe Cys Gln Ala Phe Met Asn Glu Leu Tyr Arg
                165                 170                 175

His Ile Gly Pro Cys Thr Asp Val Pro Ala Gly Asp Ile Gly Val Gly
            180                 185                 190

Gly Arg Glu Ile Gly Tyr Leu Tyr Gly Gln Tyr Lys Lys Ile Val Asn
        195                 200                 205

Ser Phe Asn Gly Thr Leu Thr Gly Lys Asn Val Lys Trp Gly Gly Ser
    210                 215                 220

Asn Leu Arg Val Glu Ala Thr Gly Tyr Gly Leu Val Tyr Phe Val Leu
225                 230                 235                 240

Glu Val Leu Lys Ser Leu Asn Ile Pro Val Glu Lys Gln Thr Ala Val
                245                 250                 255

Val Ser Gly Ser Gly Asn Val Ala Leu Tyr Cys Val Gln Lys Leu Leu
            260                 265                 270

His Leu Asn Val Lys Val Leu Thr Leu Ser Asp Ser Asn Gly Tyr Val
        275                 280                 285

Tyr Glu Pro Asn Gly Phe Thr His Glu Asn Leu Glu Phe Leu Ile Asp
    290                 295                 300

Leu Lys Glu Glu Lys Lys Gly Arg Ile Lys Glu Tyr Leu Asn His Ser
305                 310                 315                 320

Ser Thr Ala Lys Tyr Phe Pro Asn Glu Lys Pro Trp Gly Val Pro Cys
                325                 330                 335

Thr Leu Ala Phe Pro Cys Ala Thr Gln Asn Glu Ile Asn Leu Glu Asp
            340                 345                 350

Ala Lys Leu Leu Gln Lys Asn Gly Cys Ile Leu Val Gly Glu Gly Ala
        355                 360                 365

Asn Met Pro Ser Thr Val Asp Ala Ile Asn Leu Phe Lys Ser Asn Asn
    370                 375                 380

Ile Ile Tyr Cys Pro Ser Lys Ala Ala Asn Ala Gly Gly Val Ala Ile
385                 390                 395                 400

Ser Gly Leu Glu Met Ser Gln Asn Phe Gln Phe Ser His Trp Thr Arg
                405                 410                 415

Glu Thr Val Asp Glu Lys Leu Lys Glu Ile Met Arg Asn Ile Phe Ile
            420                 425                 430

Ala Cys Ser Glu Asn Ala Leu Lys Tyr Thr Lys Asn Lys Tyr Asp Leu
        435                 440                 445

Gln Ala Gly Ala Asn Ile Ala Gly Phe Leu Lys Val Ala Glu Ser Tyr
    450                 455                 460

Ile Glu Gln Gly Cys Phe
465                 470
```

MULTI-ENZYME CONJUGATE, METHOD FOR PREPARING THE SAME AND METHOD FOR PREPARING ORGANIC COMPOUND USING THE SAME

TECHNICAL FIELD

The present disclosure relates to a multi-enzyme conjugate, a method for preparing the same and a method for preparing an organic compound using the same.

BACKGROUND

In nature, multiple enzymes in one metabolic pathway often form enzyme complexes to effectively catalyze cascade reactions via intermediate channeling effect. Similarly, covalent coupling of multiple enzymes is considered a very promising strategy to enhance the enzymatic reaction efficiency for production of value-added chemicals (non-patent document 1).

Although genetic fusion and covalent coupling of enzymes using amine or thiol groups have been utilized to construct multiple-enzyme complexes (non-patent document 2), these techniques have poor control over the coupling site and crosslinking process. Coupling at multiple sites inevitably generates a mixture of enzyme conjugates with varying compositions (non-patent document 3). Furthermore, conjugation to the enzyme active site most likely compromises the catalytic activities. To enhance the control over the coupling site and enzyme-complex configuration, several elegant approaches have been developed such as co-immobilization on a DNA scaffold, residue-specific incorporation of a non-natural amino acid and enzyme-mediated conjugation (non-patent documents 1, 4 and 5). However, there were still some restrictions in choosing coupling sites.

The inventors of the present disclosure have found out that a multi-enzyme conjugate exhibiting improved catalytic efficiency over respective free enzymes can be prepared by site-specific incorporation of a clickable non-natural amino acid into the enzymes and two compatible click reactions and have completed the present disclosure.

REFERENCES OF THE RELATED ART

Non-Patent Documents (Non-patent document 1) S. Schoffelen and J. C. van Hest, *Curr. Opin. Struct. Biol.*, 2013, 23, 613-621.
(Non-patent document 2) A. H. Elcock and J. A. McCammon, *Biochemistry*, 1996, 35, 12652-12658.
(Non-patent document 3) E. Steen Redeker, D. T. Ta, D. Cortens, B. Billen, W. Guedens and P. Adriaensens, *Bioconjugate Chem.*, 2013, 24, 1761-1777.
(Non-patent document 4) J. Shimada, T. Maruyama, M. Kitaoka, H. Yoshinaga, K. Nakano, N. Kamiya and M. Goto, *Chem. Commun.*, 2012, 48, 6226-6228.
(Non-patent document 5) S. Schoffelen, J. Beekwilder, M. F. Debets, D. Bosch and J. C. M. v. Hest, *Bioconjugate Chem.*, 2013, 24, 987-996.

SUMMARY

The present disclosure is directed to providing a multi-enzyme conjugate exhibiting improved catalytic efficiency over respective free enzymes using site-specific incorporation of a clickable non-natural amino acid into the enzymes and two compatible click reactions, a method for preparing the same and a method for preparing an organic compound using the same.

The present disclosure provides a multi-enzyme conjugate including a conjugate of a first enzyme-linker and a second enzyme-linker.

The present disclosure also provides a method for preparing a multi-enzyme conjugate, including a step of coupling a first enzyme-linker with a second enzyme-linker.

The present disclosure also provides a method for synthesizing an organic compound, including a step of performing a multi-enzyme cascade reaction using the multi-enzyme conjugate according to the present disclosure.

According to the present disclosure, a multi-enzyme conjugate exhibiting improved catalytic efficiency over respective free enzymes using site-specific incorporation of a clickable non-natural amino acid into the enzymes and two compatible click reactions, a method for preparing the same and a method for preparing an organic compound using the same may be provided.

BRIEF DESCRIPTION OF DRAWINGS

FIG. 1A schematically shows two orthogonal chemical reactions, SPAAC (strain-promoted azide-alkyne cycloaddition) and IEDDA (inverse electron-demand Diels-Alder reaction), FIG. 1B schematically shows a process of constructing a multi-enzyme conjugate by the two orthogonal chemical reactions shown in FIG. 1A, and FIG. 10 schematically shows a cascade reaction using FDH (formate dehydrogenase) and MDH (mannitol dehydrogenase).

FIG. 3A schematically shows the chemical structure of AZF- and DBCO-derivatized bifunctional linkers, FIG. 3B schematically shows the structure of a FDH-MDH conjugate formed by IEDDA, and FIG. 3C shows a result of comparing the size of a FDH-MDH conjugate, wild-type FDH (FDH-WT) and wild-type MDH (MDH-WT) by size exclusion chromatography.

FIG. 4A shows a result of comparing the enzymatic activity of wild-type enzymes with those of their variants to investigate the effect of AZF incorporation on their native activity. FIG. 4B compares the D-mannitol production activity of the FDH-MDH conjugate with those of free enzymes.

FIG. 8A shows a result of subjecting a FDH-MDH conjugate corresponding to 3 nM MDH activity or a comparable amount of free FDH and MDH (3.3 nM dimeric FDH and 3 nM MDH) to a multi-enzyme cascade reaction in the presence of 500 μM NAD⁺ and 50 mM formate and D-fructose and measuring the concentration of D-mannitol products at 3 hours and 6 hours after initiation. FIG. 8B shows a result of subjecting a FDH-MDH conjugate corresponding to 10 nM MDH activity or a comparable amount of free FDH and MDH (11 nM dimeric FDH and 10 nM MDH) and measuring the concentration of mannitol products at 3 hours and 6 hours after initiation.

FIGS. 9A-9B show the amino acid sequences of FDH and MDH used in the present disclosure.

DETAILED DESCRIPTION OF EMBODIMENTS

Figure 1A:
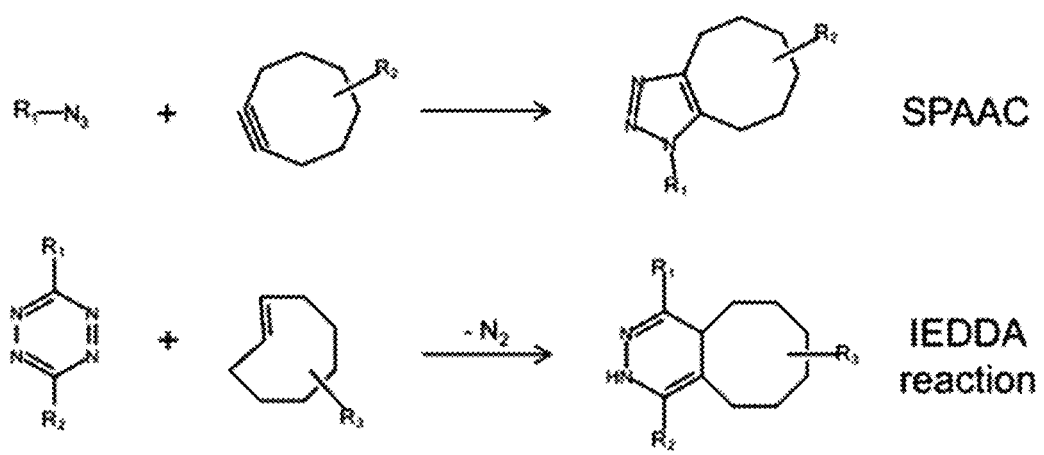
FIGS. 1A-1C schematically show a process of site-specifically coupling a multi-enzyme conjugate according to the present disclosure.

Hereinafter, various aspects and exemplary embodiments of the present disclosure are described in more detail.

In an aspect, the present disclosure relates to a multi-enzyme conjugate containing a conjugate of a first enzyme-linker and a second enzyme-linker, wherein the first enzyme-linker is a conjugate of a first modified enzyme and a first linker, the first modified enzyme contains (i) a first enzyme and (ii) one or more first non-natural amino acid (NNAA) containing a click functional group 1-1 and the first non-natural amino acid is site-specifically incorporated into a first enzyme residue of the first enzyme, the first linker contains a click functional group 1-2 and a click functional group 2-1, the first enzyme-linker is a conjugate formed from a first click reaction of the click functional group 1-1 of the first modified enzyme and the click functional group 1-2 of the first linker, the second enzyme-linker is a conjugate of a second modified enzyme and a second linker, the second linker contains a click functional group 2-2 and a click functional group 3-1, the second modified enzyme contains (i) a second enzyme and (ii) one or more second non-natural amino acid containing a click functional group 3-2 and the second non-natural amino acid is site-specifically incorporated into a second enzyme residue of the second enzyme, the second enzyme-linker is a conjugate formed from a third click reaction of the click functional group 3-1 of the second linker and the click functional group 3-2 of the second modified enzyme, and the conjugate of the first enzyme-linker and the second enzyme-linker is a conjugate formed from a second click reaction of the click functional group 2-1 of the first linker and the click functional group 2-2 of the second linker.

The present disclosure is advantageous in that the distance between enzymes can be controlled by locating a linker between the enzymes and the flexibility, solubility and reversibility of the resulting conjugate can be controlled by varying the length and characteristics of the linker.

In the present disclosure, "site-specifically incorporated into an enzyme residue" means that the non-natural amino acid is incorporated only into the corresponding enzyme residue, not into other sites. The non-natural amino acid can be introduced to any site of the enzyme and the non-natural amino acid may be used as a coupling site. For example, the enzyme may be FDH or MDH and the residue may be the residue introduced into the non-natural amino acid described in the examples. However, the scope of the present disclosure is not reduced or limited by them.

In an exemplary embodiment, in a multi-enzyme cascade reaction including a first enzymatic reaction and a second enzymatic reaction wherein a product of the first enzymatic reaction is used as a reactant of the second enzymatic reaction, the first enzyme acts as a biocatalyst of the first enzymatic reaction and the second enzyme acts as a biocatalyst of the second enzymatic reaction.

The multi-enzyme cascade reaction applicable to the present disclosure is not particularly limited and includes the reactions described in Ricca, Emanuele, Birgit Brucher, and Joerg H. Schrittwieser. "Multi-enzyme cascade reactions: overview and perspectives." *Advanced Synthesis & Catalysis* 353.13 (2011): 2239-2262 and elsewhere.

In another exemplary embodiment, the first enzyme and the second enzyme are a pair selected from FDH and MDH, MDH and FDH, FDH and ADH, ADH and FDH, NOX and ADH, ADH and NOX, LDH and HSDH, HSDH and LDH, GDM and 7β-HSDH, 7β-HSDH and GDM, ADH and halohydrin dehalogenase, halohydrin dehalogenase and ADH, GDH and ketoreductase, ketoreductase and GDH, BVMO and ADH, ADH and BVMO, LDH and AlaDH, AlaDH and LDH, FDH and PheDH, PheDH and FDH, NOX and LeuDH, LeuDH and NOX, FDH and LeuDH, LeuDH and FDH, GOT and TA, TA and GOT, FDH and AlaDH, AlaDH and FDH, FDH and GluDH, and GluDH and FDH, respectively.

In the present disclosure, FDH refers to formate dehydrogenase (exemplified by SEQ ID No.: 1), MDH refers to mannitol dehydrogenase (exemplified by SEQ ID No.: 2), ADH refers to alcohol dehydrogenase (exemplified by SEQ ID No: 3), NOX refers to NADH oxidase (exemplified by SEQ ID No.: 4), LDH refers to lactate dehydrogenase (exemplified by SEQ ID No.: 5), HSDH refers to hydroxysteroid dehydrogenase (exemplified by SEQ ID No.: 6), GDM refers to glutamate dehydrogenase (exemplified by SEQ ID No.: 7), 7β-HSDH refers to 7-beta-Hydroxysteroid Dehydrogenase (exemplified by SEQ ID No.: 8), HheA refers to Halohydrin Dehalogenase (SEQ ID No.: 9), GDH refers to glucose dehydrogenase (SEQ ID No. 10), Ketoreductase is exemplified by SEQ ID No. 11, BVMO refers to Baeyer-Villiger monooxygenase (SEQ ID No.: 12), AlaDH refers to alanine dehydrogenase (SEQ ID No.: 13), PheDH refers to phenylalanine dehydrogenase (SEQ ID No.: 14), LeuDH refers to L-leucine dehydrogenase (SEQ ID No.: 15), GOT refers to glutamate oxaloacetate transaminase (exemplified by SEQ ID No. 16), TA refers to α-transaminase (exemplified by SEQ ID No. 17), and GluDH refers to glutamate dehydrogenase (exemplified by SEQ ID No. 18).

Although amino acid sequences of the enzymes are listed in Sequence Listing, the listed amino acid sequences of enzymes are merely representative amino acid sequences of each enzyme. The sequence of each enzyme may vary depending on the species (animal, plant or microorganism) from which the enzyme is derived. Thus, the amino acid sequences of the respective enzymes listed in Sequence Listing are merely exemplary, and the scope of the instant disclosure should not be interpreted as being limited to the listed amino acid sequences.

In particular, the HSDH is 7α-HSDH or 12α-HSDH, and the TA is (4-AB:2-KG)TA.

In another exemplary embodiment, the first enzyme residue and the second enzyme residue are identical to or different from each other and respectively contain one or more hydrophobic side chain selected from phenylalanine, tryptophan and valine.

In another exemplary embodiment, the first enzyme residue and the second enzyme residue have a solvent accessibility of 0.4-1. In the present disclosure, the "solvent accessibility" means the ASA value measured by the web-based program ASA-View. If the solvent accessibility is lower than 0.4, the tendency of coupling with a linker may be low.

In another exemplary embodiment, the first non-natural amino acid containing the click functional group 1-1 and the second non-natural amino acid containing the click functional group 3-2 are identical to or different from each other and are respectively selected from p-azido-L-phenylalanine (AZF), p-ethynyl-phenylalanine (pEthF) and p-propargyloxyphenylalanine (pPa).

In another exemplary embodiment, the first enzyme and the second enzyme are respectively FDH and MDH, and the first enzyme residue and the second enzyme residue are respectively valine at position 237 and valine at position 417. Specifically, the numbering of the residue site of the MDH may be determined according to the method of Brunker et al., BBA, 1997. Details can be found in FIG. 9.

In another exemplary embodiment, the second click reaction and the first click reaction are orthogonal to each other and are orthogonal to the third click reaction.

In the present disclosure, "orthogonal chemical reactions" mean reactions occurring independently of each other with no effect on each other.

In another exemplary embodiment, the first click reaction and the second click reaction are an orthogonal reaction pair such as SPAAC and IEDDA, IEDDA and SPAAC, SPAAC and carbonyl ligation, carbonyl ligation and SPAAC, IEDDA and carbonyl ligation, carbonyl ligation and IEDDA, carbonyl ligation and photoactivated ligation, photoactivated ligation and carbonyl ligation, etc. respectively.

In another exemplary embodiment, the SPAAC refers to strain-promoted azide-alkyne cycloaddition, the IEDDA refers to reverse electron-demand Diels-Alder reaction, and CuAAC refers to copper-catalyzed azide-alkyne cycloaddition.

In another exemplary embodiment, the click functional group 1-1 and the click functional group 1-2, and the click functional group 3-1 and the click functional group 3-2 are respectively a pair selected from azido ($N_3$) and strain-promoted alkyne (C≡C), strain-promoted alkyne and azido, azido and alkyne, alkyne and azido, tetrazine and trans-cyclooctene, trans-cyclooctene and tetrazine, aldehyde and aminooxy, aminooxy and aldehyde, aldehyde and hydrazine, hydrazine and aldehyde, ketone and aminooxy, aminooxy and ketone, ketone and hydrazine, hydrazine and ketone, tetrazole and alkyne, and alkyne and tetrazole.

The click functional group 2-1 and the click functional group 2-2 should be functional groups lacking binding ability with the click functional group 1-1, the click functional group 1-2, the click functional group 3-1 and the click functional group 3-2. They are respectively a pair selected from azido ($N_3$) and strain-promoted alkyne (C≡C), strain-promoted alkyne and azido, azido and alkyne, alkyne and azido, tetrazine and trans-cyclooctene, trans-cyclooctene and tetrazine group, aldehyde and aminooxy, aminooxy and aldehyde, aldehyde and hydrazine, hydrazine and aldehyde, ketone and aminooxy, aminooxy and ketone, ketone and hydrazine, hydrazine and ketone, tetrazole and alkyne, and alkyne and tetrazole.

In another exemplary embodiment, the strain-promoted alkyne is cyclooctyne.

In another exemplary embodiment, the click functional group 1-1 and the click functional group 1-2 are respectively tetrazine and trans-cyclooctene (or trans-cyclooctene and tetrazine), the click functional group 3-1 and the click functional group 3-2 are respectively tetrazine and trans-cyclooctene (or trans-cyclooctene and tetrazine), and the click functional group 2-1 and the click functional group 2-2 are respectively azido and alkyne (C≡C) (or alkyne and azido).

In another exemplary embodiment, the click functional group 1-1 and the click functional group 1-2 are respectively azido and alkyne (C≡C) (or alkyne and azido), the click functional group 3-1 and the click functional group 3-2 are respectively azido and alkyne (C≡C) (or alkyne and azido), and the click functional group 2-1 and the click functional group 2-2 are respectively tetrazine and trans-cyclooctene (or trans-cyclooctene tetrazine).

In another exemplary embodiment, the click functional group 1-1 and the click functional group 1-2 are respectively azido and alkyne, the click functional group 3-1 and the click functional group 3-2 are respectively alkyne and azido, and the click functional group 2-1 and the click functional group 2-2 are respectively tetrazine and trans-cyclooctene.

In another exemplary embodiment, the first modified enzyme is FDH-AZF, the first linker contains DBCO and tetrazine at both ends, the second linker contains DBCO and TCO at both ends, and the second modified enzyme is MDH-AZF.

In the present disclosure, DBCO refers to dibenzocyclooctyne and TCO refers to trans-cyclooctene.

In another exemplary embodiment, the first linker is a compound of the following structure:

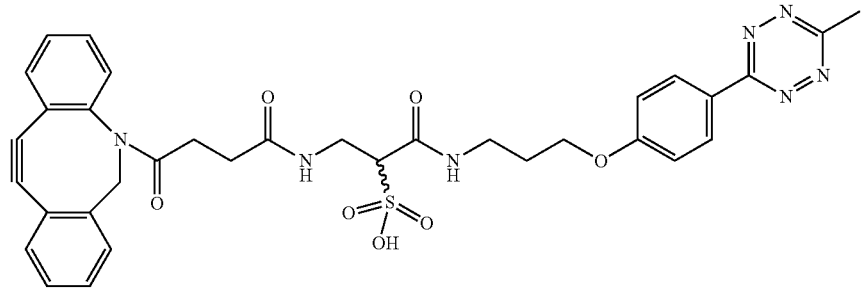 [SMILES: Cc1nnc(-c2ccc(OCCCNC(=O)C(CNC(=O)CCC(=O)N3Cc4ccccc4C#Cc4ccccc43)S(=O)(=O)O)cc2)nn1]

and the second linker is a compound of the following structure:

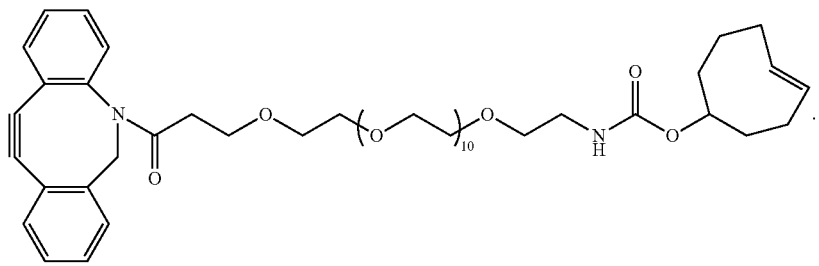

In another exemplary embodiment, the multi-enzyme conjugate has the following structure.

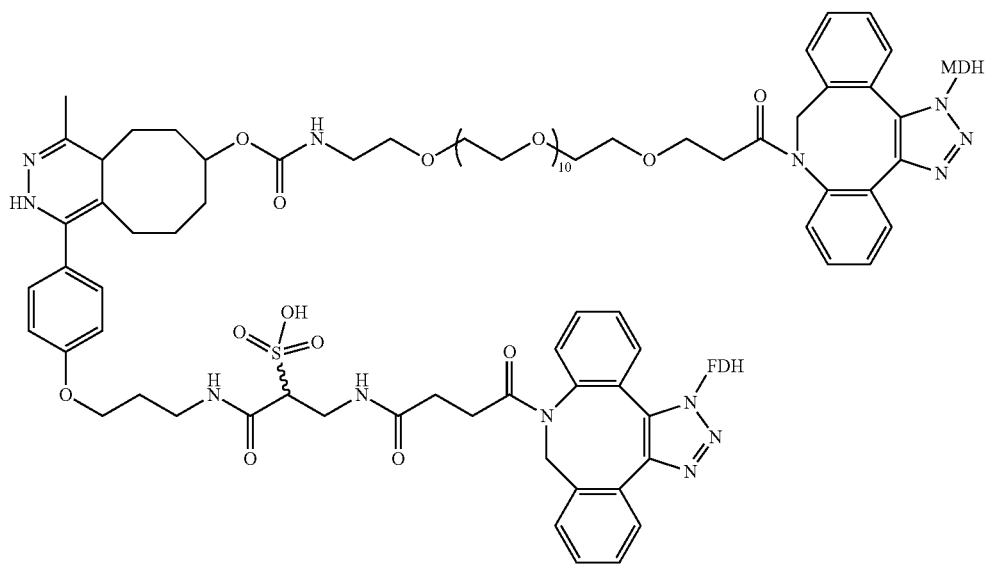

In another aspect, the present disclosure relates to a method for preparing a multi-enzyme conjugate, including (C) a step of coupling a first enzyme-linker with a second enzyme-linker, wherein the first enzyme-linker is a conjugate of a first modified enzyme and a first linker, the first modified enzyme contains (i) a first enzyme and (ii) one or more first non-natural amino acid (NNAA) containing a click functional group 1-1 and the first non-natural amino acid is site-specifically incorporated into a first enzyme residue of the first enzyme, the first linker contains a click functional group 1-2 and a click functional group 2-1, the first enzyme-linker is a conjugate formed from a first click reaction of the click functional group 1-1 of the first modified enzyme and the click functional group 1-2 of the first linker, the second enzyme-linker is a conjugate of a second modified enzyme and a second linker, the second linker contains a click functional group 2-2 and a click functional group 3-1, the second modified enzyme contains (i) a second enzyme and (ii) one or more second non-natural amino acid containing a click functional group 3-2 and the second non-natural amino acid is site-specifically incorporated into a second enzyme residue of the second enzyme, the second enzyme-linker is a conjugate formed from a third click reaction of the click functional group 3-1 of the second linker and the click functional group 3-2 of the second modified enzyme, and the step (C) is performed by a second click reaction of the click functional group 2-1 of the first linker and the click functional group 2-2 of the second linker.

In another aspect, the present disclosure relates to a method for preparing a multi-enzyme conjugate, including (B1) a step of obtaining a first enzyme-linker by coupling a first modified enzyme with a first linker, (B2) a step of obtaining a second enzyme-linker by coupling a second modified enzyme with a second linker, and (C) a step of coupling the first enzyme-linker with the second enzyme-linker, wherein the first modified enzyme contains (i) a first enzyme and (ii) one or more first non-natural amino acid (NNAA) containing a click functional group 1-1 and the first non-natural amino acid is site-specifically incorporated into a first enzyme residue of the first enzyme, the first linker contains a click functional group 1-2 and a click functional group 2-1, the step (B1) is performed by a first click reaction of the click functional group 1-1 of the first modified enzyme and the click functional group 1-2 of the first linker, the second linker contains a click functional group 2-2 and a click functional group 3-1, the second modified enzyme contains (i) a second enzyme and (ii) one or more second non-natural amino acid containing a click functional group 3-2 and the second non-natural amino acid is site-specifically incorporated into a second enzyme residue of the second enzyme, the step (B2) is performed by a third click reaction of the click functional group 3-1 of the second linker and the click functional group 3-2 of the second modified enzyme, and the step (C) is performed by a second click reaction of the click functional group 2-1 of the first linker and the click functional group 2-2 of the second linker.

In another aspect, the present disclosure relates to a method for preparing a multi-enzyme conjugate, including (A1) a step of obtaining a first modified enzyme by site-specifically replacing one or more first enzyme residue of a first enzyme with a first non-natural amino acid containing a click functional group 1-1, (A2) a step of obtaining a second modified enzyme by site-specifically replacing one or more second enzyme residue of a second enzyme with a second non-natural amino acid containing a click functional group 3-2, (B1) a step of obtaining a first enzyme-linker by coupling the first modified enzyme with a first linker, (B2) a step of obtaining a second enzyme-linker by coupling the second modified enzyme with a second linker, and (C) a step of coupling the first enzyme-linker with the second enzyme-linker, wherein the first linker contains a click functional group 1-2 and a click functional group 2-1, the step (B1) is performed by a first click reaction of the click functional group 1-1 of the first modified enzyme and the click functional group 1-2 of the first linker, the second linker contains a click functional group 2-2 and a click functional group 3-1, the step (B2) is performed by a third click reaction of the click functional group 3-1 of the second linker and the click functional group 3-2 of the second modified enzyme, and the step (C) is performed by a second click reaction of the click functional group 2-1 of the first linker and the click functional group 2-2 of the second linker.

An expanded genetic code has brought a breakthrough in linking proteins. It allows site-specific incorporation of a non-natural amino acid into a target protein at any site, in *E. coli*, yeast and animal cells. A reactive non-natural amino acid serves as a chemical handle and allows linking of a molecule having a functional group of the same origin with another natural amino acid without crosstalk.

In the present disclosure, a non-natural amino acid may be introduced into a specific protein site using a specially modified orthogonal tRNA/aminoacyl-tRNA synthetase pair. In general, the amber stop codon is used to introduce a non-natural amino acid into a specific site of a target protein. By using genomically amber-free *E. coli*, in which release factor 1 is knocked out, and inserting an amber codon at a desired site, it is possible to introduce anon-natural amino acid into the site. Details can be referred to literatures such as *Journal of Controlled Release* 207 (2015) 93-100 ("Site-specific albumination of a therapeutic protein with multi-subunit to prolong activity in vivo").

In another aspect, the present disclosure relates to a method for synthesizing an organic compound, including a step of performing a multi-enzyme cascade reaction using the multi-enzyme conjugate according to the various aspects of the present disclosure, wherein the multi-enzyme cascade reaction includes a first enzymatic reaction and a second enzymatic reaction, a product of the first enzymatic reaction is used as a reactant of the second enzymatic reaction, the first enzyme of the multi-enzyme conjugate acts as a biocatalyst of the first enzymatic reaction, and the second enzyme of the multi-enzyme conjugate acts as a biocatalyst of the second enzymatic reaction.

In an exemplary embodiment, the first enzymatic reaction and the second enzymatic reaction are a pair selected from the following reaction pairs:

[Scheme 1a]

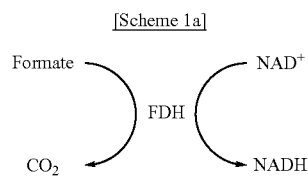

[Scheme 1b]

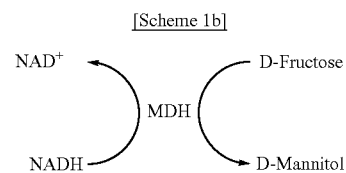

[Scheme 1c]

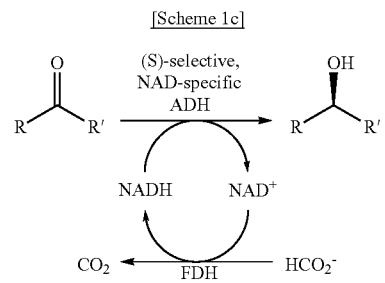

[Scheme 1d]

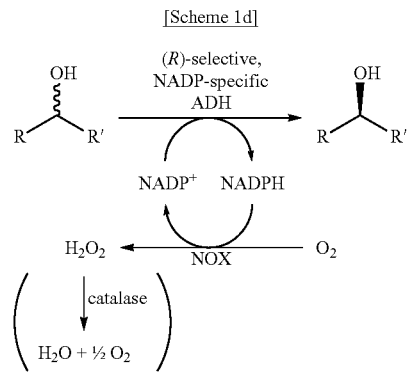

[Scheme 1e]
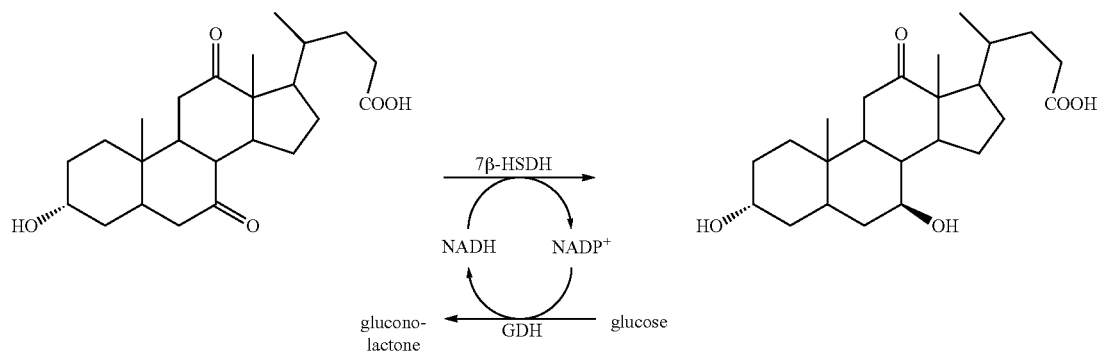
[Scheme 1f]
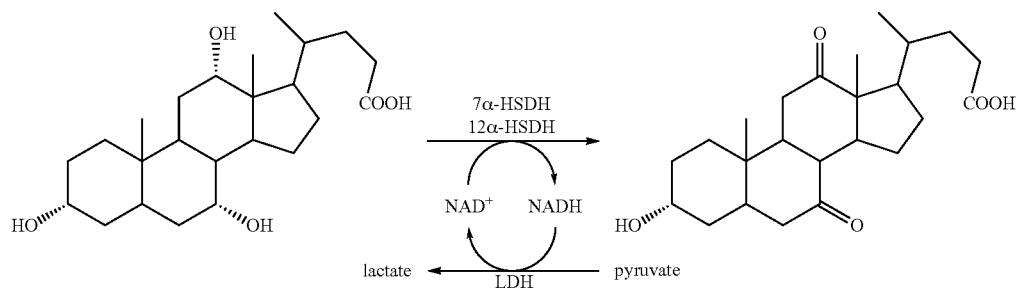
[Scheme 1g]
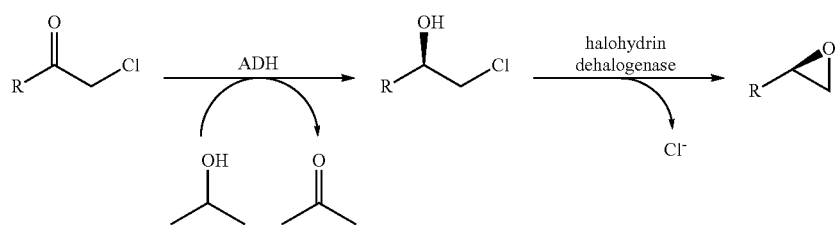
[Scheme 1h]
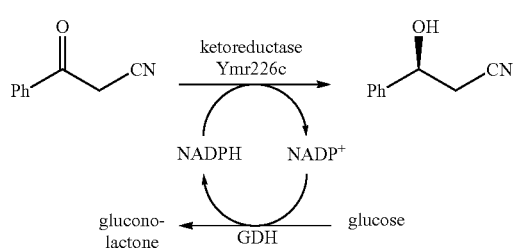
[Scheme 1i]
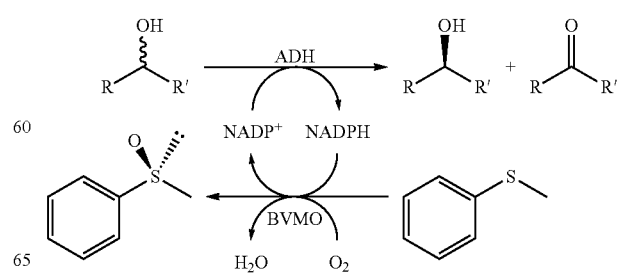

[Scheme 1j]
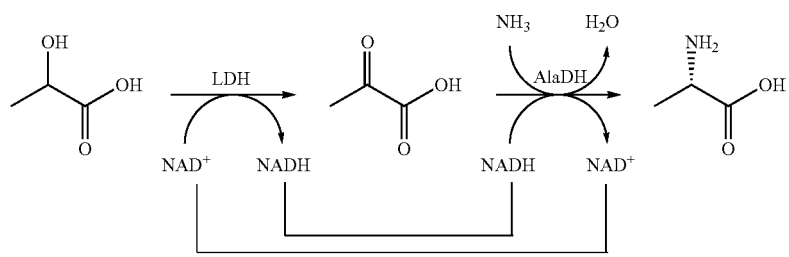
[Scheme 1k]
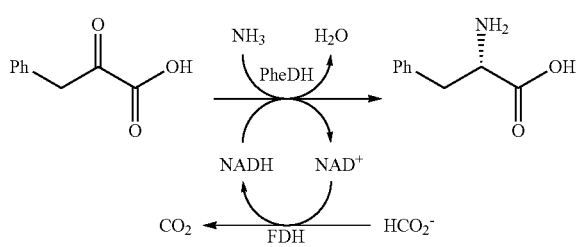
[Scheme 1n]
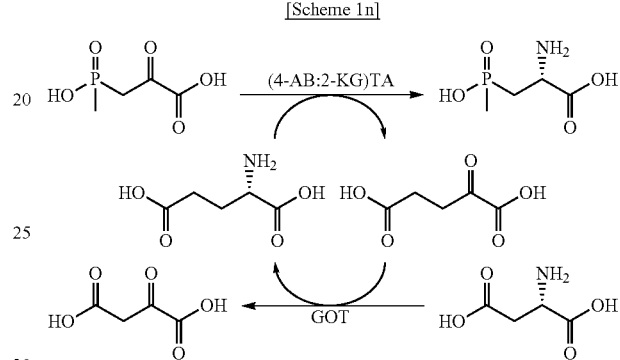
[Scheme 1l]
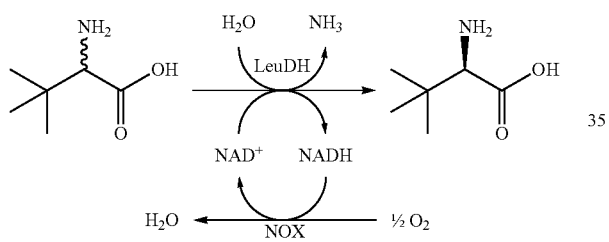
[Scheme 1m]
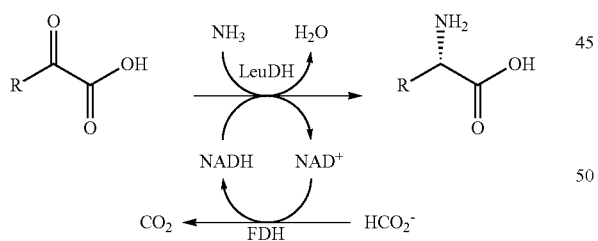
[Scheme 1o]
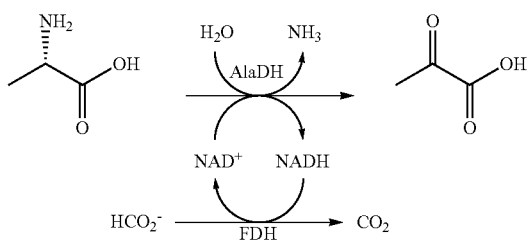
[Scheme 1p]
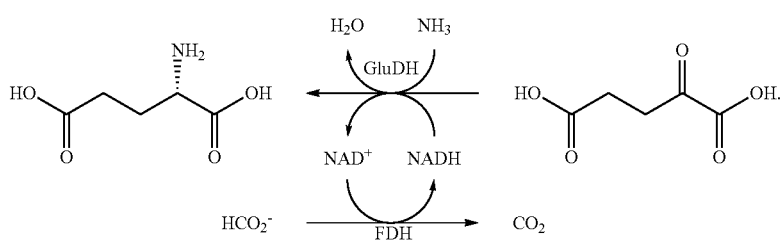

In another exemplary embodiment, the first enzymatic reaction is the following reaction:

[Scheme 1a]

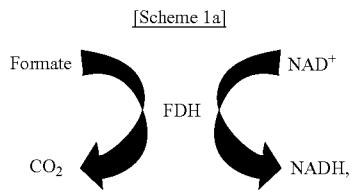

the second enzymatic reaction is the following reaction:

[Scheme 1b]

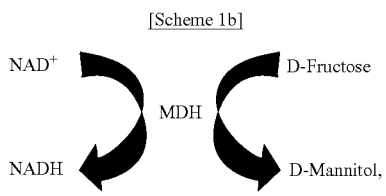

and the organic compound is D-mannitol.

In an exemplary embodiment of the present disclosure, urate oxidase (Uox) may be coupled with human serum albumin (HSA). Because various enzymatic activities are known for HSA, the binding between Uox and has may be seen as an enzyme-enzyme binding. After introducing p-azido-phenylalanine into urate oxidase (Uox) and coupling a DBCO-maleimide linker to free Cys34 of HSA, the Uox-$N_3$ and the DBCO-has are coupled through click chemistry.

In another exemplary embodiment of the present disclosure, superfolder green fluorescent protein (sfGFP) may be coupled with HSA or mouse serum albumin in a similar manner. Although sfGFP is not an enzyme in a strict sense, it may be included in the enzymes of the present disclosure because it is a protein having activity.

In another exemplary embodiment of the present disclosure, by introducing a non-natural amino acid containing a tetrazine group to sfGFP, Uox or MDH, it may be coupled with an enzyme containing an azido group through click chemistry using a DBCO-TCO linker.

The following literatures are incorporated in the present disclosure in their entirety.
Korean Patent Application No. 10-2015-0058164.
*Journal of Controlled Release* 207 (2015) 93-100.
*Chem. Comm.* 2015.
*Scientific Reports* 2016.

Exemplary embodiments now will be described more fully hereinafter with reference to Examples and Test Example. The present disclosure may, however, be embodied in many different forms and should not be construed as limited to the exemplary embodiments set forth therein. While the present disclosure has been described with respect to the specific embodiments, it will be apparent to those skilled in the art that various changes and modifications may be made without departing from the spirit and scope of the disclosure as defined in the following claims.

In addition, the following test results are typical test results of Examples and Comparative Examples. Each of the effects of various embodiments not specified hereinafter will be described particularly at the corresponding part.

Reference Example p-Azido-L-phenylalanine (AZF) was obtained from Chem-Impex International (Wood Dale, Ill.). DBCO-$PEG_4$-carboxyrhodamine and DBCO-PEG12-TCO (trans-cyclooctene) were purchased from Bioconjugate Technology Company (Scottsdale, Ariz.). Ni-nitrilotriacetic acid (NTA) agarose and pQE80 plasmid were purchased from Qiagen (Valencia, Calif.). ZipTip C18 and Vivaspin centrifugal concentrators with a MWCO (molecular weight cut-off) of 50 kDa were purchased from Millipore Corporation (Billerica, Mass.) and Sartorius Corporation (Bohemia, N.Y.), respectively. Sequencing grade-modified trypsin was purchased from Promega Corporation (Madison, Wis.). The UNO Q1 anion exchange column and the Biologic DuoFlow chromatography system were purchased from Bio-Rad (Hercules, Calif.). The Superdex 200 10/300 GL size exclusion column, the HiTrap SP HP cation exchange column and the PD-10 desalting column were obtained from GE Healthcare (Piscataway, N.J.). All chemicals were obtained from Sigma-Aldrich (St. Louis, Mo.) unless stated otherwise.

Example 1: Plasmid Construction and Strains

A plasmid pEVOL-pAZF encoding an AZF-specific engineered pair of tyrosyl-tRNA synthase/amber suppressor tRNA derived from *Methanococcus jannaschii* (plasmid ID: 31186) was obtained from Addgene (Cambridge, Mass.) and used without modification. A pQE-80 TsFDH plasmid encoding the fdh gene was originally obtained from *Thiobacillus* sp. KNK65MA, with an additional C-terminal histidine sequence, was prepared by the known method. Site-directed mutagenic PCR was performed with pQE80-FDH as a template to replace the valine codon at position 237 with amber codons (UAG), yielding pQE80-FDH-V237amb, respectively.

*E. coli* TOP10 was transformed with pQE80-FDH for expression of the wild-type FDH (FDH-WT), affording TOP10 [FDH-WT].

As an expression host for AZF-incorporated FDH (FDH-V237AZF), genomically engineered *E. coli* C321.ΔA.exp was obtained from Addgene (ID: 49018) and co-transformed with pEVOL-pAZF and pQE80-FDH-V237amb, affording C321.ΔA.exp [FDHV237amb], respectively.

The mdh gene, which encodes mannitol-2-dehydrogenase originating from *Pseudomonas fluorescens*, with an additional C-terminal histidine sequence was synthesized by GenScript (Piscataway, N.J.) and subcloned into pQE80 to generate pQE80-MDH. Site-directed mutagenic PCR was performed with pQE80-MDH as a template to replace the valine codon at position 417 with an amber codon (UAG), yielding pQE80-MDH-V417amb.

*E. coli* TOP10 was transformed with pQE80-MDH for expression of the wild-type MDH (MDH-WT), affording TOP10 [MDH-WT]. As an expression host for AZF-incorporated MDH (MDH-AZF), genomically engineered *E. coli* 0321.ΔA.exp was co-transformed with pEVOL-pAZF and pQE80-MDH-V417amb, affording 0321.ΔA.exp [MDH-V417amb].

All DNA cloning was performed by the restriction-free cloning technique.

Example 2: Site-Specific Incorporation of AZF into FDH and MDH

A saturated culture of 0321.ΔA.exp [FDH-V237amb or MDH-V417amb] was inoculated into a fresh 2×YT medium containing 100 µg/mL ampicillin and 35 µg/mL chloramphenicol at 1:100 (v/v) dilution and was subjected to vigorous shaking (220 rpm) at 37° C.

When the OD600 of 0.5 was reached, the AZF solution was added to a final concentration of 1 mM. After 30 minutes, temperature was shifted to 30° C. and protein expression was induced by 1 mM IPTG and 0.2% (w/v) L-(+)-arabinose. Cells were harvested after 12 hours and pelleted by centrifugation at 5,000 rpm for 10 minutes before storage at 20° C.

To extract and purify FDH or MDH containing AZF, cell pellets were resuspended with a lysis buffer consisting of 50 mM sodium phosphate (pH 7.5), 0.3 M sodium chloride, 10 mM imidazole, 1 mg/mL lysozyme, DNase (deoxyribonuclease), RNase (ribonuclease) and protease inhibitor cocktail and mixed by rotation at 37° C. for 1 hour followed by at 4° C. for 2 hours. After centrifugation at 11,000 rpm for 30 minutes, the supernatant was recovered, mixed with Ni-NTA agarose for 1 hour and then washed with a washing buffer consisting of 50 mM sodium phosphate (pH 7.5), 0.3 M sodium chloride and 20 mM imidazole on a gravity flow column to remove impurities.

Proteins were eluted by an elution buffer consisting of 50 mM sodium phosphate (pH 7.5), 0.3 M sodium chloride and 250 mM imidazole and then buffer-exchanged to a storage buffer (PBS, pH 7.2) by a PD-10 column. Expression and purification of FDH-WT or MDH-WT were performed similarly except that TOP10 [FDH-WT or MDH-WT] was used as an expression host without adding AZF and L-(+)-arabinose.

Example 3: Synthesis of FDH-MDH Conjugate

First, hetero-bifunctional linkers, DBCO-tetrazine and DBCO-PEG12-TCO were conjugated to FDH-AZF and MDH-AZF by SPAAC to generate FDH-TET and MDH-TCO, respectively. Second, the FDH-TET was conjugated to MDH-TCO by IEDDA reaction. Lastly, the FDH-MDH conjugate was purified by ion exchange liquid chromatography.

Detailed conditions are as follows. FDH-AZF was mixed with 4 molar excess of DBCO-tetrazine in PBS containing 5% (v/v) DMSO and reacted at room temperature for 7 hours. To remove residual DBCO-tetrazine, the reaction mixture was desalted on a PD-10 column and buffer-exchanged to a 20 mM bis-tris buffer at pH 6.0. MDH-AZF was similarly treated except that DBCO-PEG12-TCO was used instead of DBCO-tetrazine. FDH-TET and MDH-TCO thus obtained were mixed at 1:1 molar stoichiometry, concentrated to a total protein concentration of 5 mg/mL and reacted at room temperature for 1 hour.

The reaction mixture was directly loaded onto an anion exchange column, UNO Q1, pre-equilibrated with a 20 mM bis-tris buffer (pH 6.0) and resolved by applying a NaCl gradient. A fraction containing the FDH-MDH conjugate was collected and characterized on a size exclusion column, Superdex 200, to estimate its size and purity.

Test Example 1: MALDI-TOF Mass Spectrometry

Proteins in the storage buffer at 0.5 mg/mL were digested with trypsin at 37° C. overnight and then desalted on ZipTip C18 according to the manufacturer's protocol. Purified tryptic digests mixed with a DHB matrix (20 mg/mL of 2,5-dihydroxybenzoic acid and 2 mg/mL of L(−)-fucose dissolved in 10% ethanol) at 1:1 (v/v) were subjected to mass characterization by Microflex MALDI-TOF M/S (Bruker Corporation, Billerica, Mass.).

Test Example 2: Dye Labeling by SPACC

FDH-WT, MDH-WT and their variants at 30 µM in a storage buffer were separately reacted with DBCO-PEG$_4$-carboxyrhodamine at 100 µM at room temperature for 2 hours and then loaded onto SDS-PAGE to measure in-gel fluorescence in a BioSpectrum imaging system (UVP, Upland, Calif.). Upon illumination at $\lambda_{ex}$=480 nm, the emitted light above 510 nm was captured.

Test Example 3: Enzymatic Activity Assay

The enzymatic activity of FDH-WT and its variants was measured by formate oxidation to $CO_2$. The reaction was initiated by mixing 5 µL of 400 nM FDH-WT or its variant with 195 µL of an assay buffer consisting of 50 mM formate and 300 µM NAD$^+$ in PBS and then monitored at A340 nm.

The enzymatic activity of MDH-WT and its variants was measured by D-fructose reduction to D-mannitol. The reaction was initiated by mixing 5 µL of 40 nM MDHWT or its variant with 195 µL of an assay buffer consisting of 50 mM D-fructose and NADH in PBS and then monitored at A340 nm.

All measurements were made in triplicate at 25° C. in a standard 96-well plate on the Synergy™ 4-multimode microplate reader (BioTek, Winooski, Vt.). The change in absorbance after 1 minute was taken as a measure of catalytic activity.

Test Example 4: Determination of Molar Composition of FDH-MDH Conjugate

Calibration curves for determining the molar composition of the FDH-MDH conjugate based upon respective catalytic activities were constructed by plotting absorbance change at A340 nm for 1 minute, i.e., the slope upon initiation of enzymatic reactions as described above except that enzyme concentrations were varied: 100, 200, and 400 nM for FDH; 5, 10, 20 nM for MDH. Linear regression was applied to express enzyme concentrations as a linear function of A340 nm slopes.

An appropriate volume of the FDH-MDH conjugate solution was individually subjected to both enzymatic activities under the same conditions to obtain A340 nm slopes, which was then fit to linear functions to estimate molar concentrations of FDH and MDH.

Test Example 5: Measurement of D-Mannitol Production in Enzymatic Cascade Reaction A cascade reaction was initiated by mixing 10 µL of the FDH-MDH conjugate (50× working concentration) or a free enzyme mix of wild-type FDH (FDH-WT) and wild-type MDG (MDH-WT) with 490 µL of an assay solution consisting of 50 mM formate, 50 mM D-fructose and 500 µM NAD$^+$ in PBS. At appropriate time points, 150 µL of the reaction mixture were sampled in separate tubes. After lowering pH to 3.0 by adding hydrochloric acid, the sample was heated at 80° C. for 40 minutes to inactivate enzymes and residual cofactors.

Enzymatic D-mannitol assay was conducted to measure the amount of D-mannitol in the sample by mixing 40 µL and 160 µL of an assay solution consisting of 50 nM MDH-WT and 600 µM NAD$^+$ in sodium bicarbonate buffered at pH 9.5 and monitoring increase in A340 nm attributed by enzymatic oxidation of D-mannitol to D-fructose.

Figure 7:
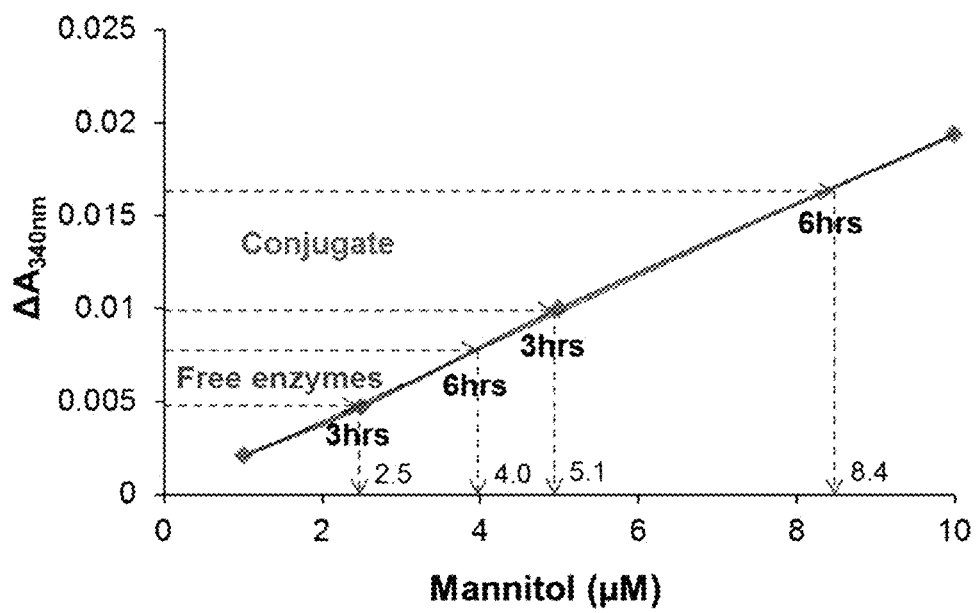
FIG. 7 shows a result of analyzing mannitol concentration in the presence of a FDH-MDH conjugate synthesized in Example 3, free FDH and free MDH.

The absorbance change for 5 minutes was used to calculate the concentration of D-mannitol in the sample by fitting to a D-mannitol calibration curve which was obtained in advance by performing the D-mannitol assay using a known amount of D-mannitol (1.0, 2.5, 5.0 and 10 μM) and by relating the absorbance change for 5 minutes to D-mannitol concentrations by linear regression [FIG. 7]. All measurements were made in triplicate.

A more detailed description is given referring to the attached drawings.

Figure 1B:
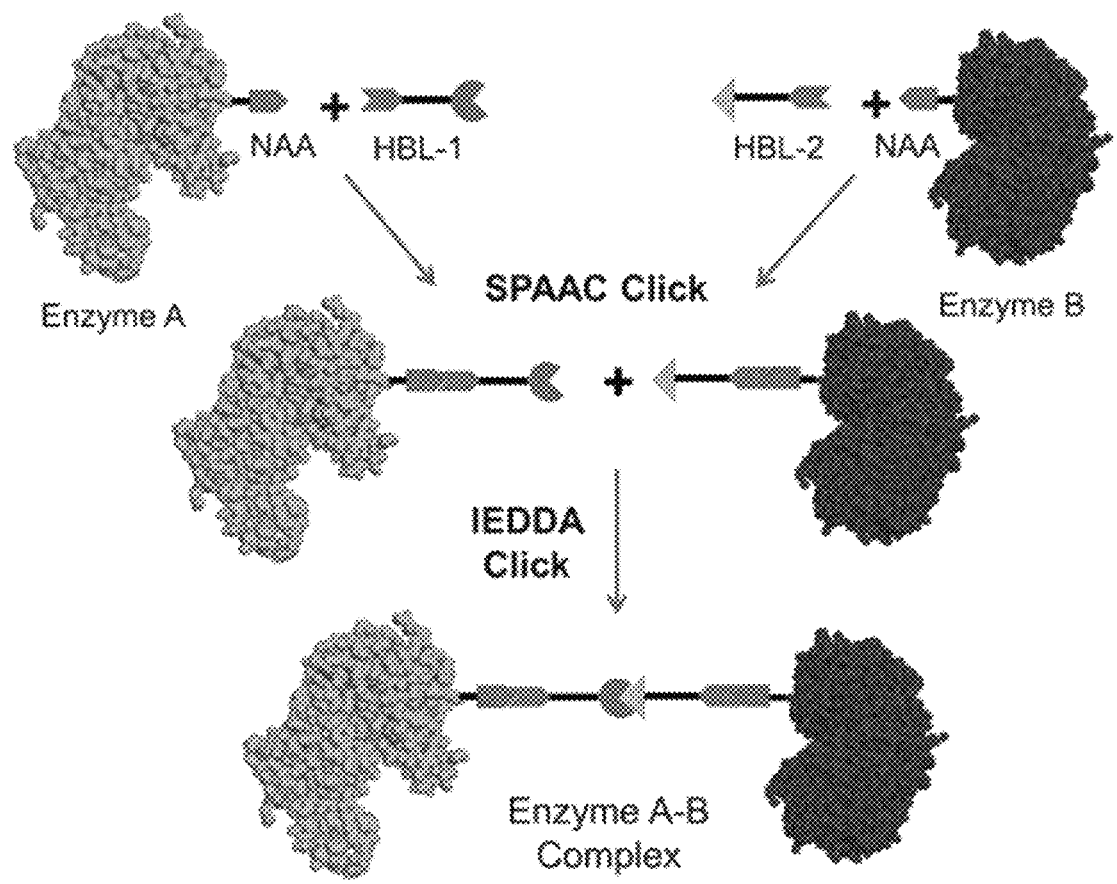
Figure 1C:
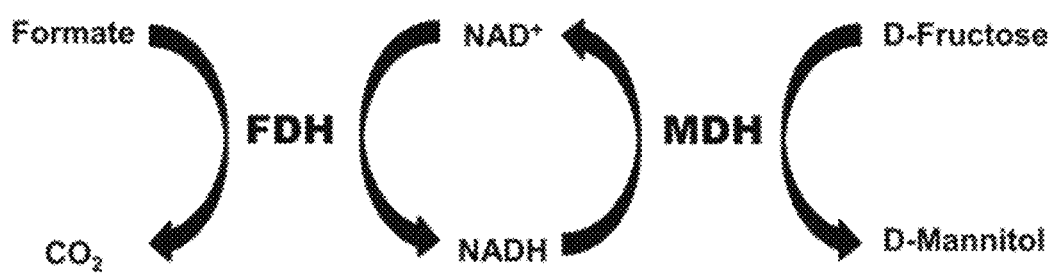

First, a clickable p-azido-L-phenylalanine (AZF) was introduced into two enzymes (enzymes A and B) with retained catalytic activity. Then, two clickable hetero-bifunctional linkers (HBL-1 and HBL-2) were conjugated to two different enzymes via a first click reaction, SPAAC (strain-promoted azide-alkyne cycloaddition). Finally, the two enzyme-linker conjugates were coupled via a second click reaction, IEDDA (inverse electron demand Diels-Alder reaction), to generate a multi-enzyme reaction system [see FIG. 1B].

Recently, site-specific conjugation of enzymes has received great attention, because enzyme conjugation can be made at permissive sites. Once a clickable non-natural amino acid is introduced into an enzyme, a click reaction, such as CuAAC (copper-catalyzed azide-alkyne cycloaddition) or SPAAC, is employed to immobilize the enzyme onto a solid surface. When a conjugation site is carefully chosen, the enzyme retains catalytic activity even after the conjugation. Bundy et al. previously reported the introduction of two clickable non-natural amino acids, namely, p-propargyloxy-L-phenylalanine and p-azido-L-phenylalanine, into two different proteins for direct protein-to-protein conjugation via CuAAC click reaction.

Despite its simplicity and site specificity of coupling, the application of this technique to enzymes seems limited due to a potential issue of activity loss caused by copper ions. Thus, in the present disclosure, site-specific coupling of multiple enzymes was achieved via two consecutive click reactions to generate absolute site specificity in the coupling site while retaining the enzyme activity [see FIG. 1B].

As a model system, a pair of formate dehydrogenase (FDH) and mannitol dehydrogenase (MDH) was chosen. FDH is a homodimer with a molecular mass of 45 kDa for a single subunit originating from *Thiobacillus* sp. KNK65MA, and catalyzes the conversion of formate into carbon dioxide by reducing the cofactor $NAD^+$ to NADH. MDH, derived from *Pseudomonas fluorescens*, is a monomer with a molecular mass of 55 kDa and catalyzes the reduction of D-fructose to D-mannitol by consuming NADH. In cascade reactions consisting of FDH and MDH, NADH is regenerated by FDH-catalyzed formate oxidation, thereby continuously fueling MDH-catalyzed D-mannitol production. In the presence of excess substrates, namely, formate and D-fructose, for both enzymes, the transfer of NADH between the active sites of FDH and MDH governs the overall cascade reaction efficiency [see FIG. 10].

As a first step to construct FDH-MDH conjugates, conjugation sites were carefully chosen. Several factors were taken into consideration. First, to avoid activity loss upon coupling, coupling sites should not be involved in a native function. Second, to minimize the structural perturbation upon incorporation of AZF, residues with a hydrophobic side chain, such as phenylalanine, tryptophan and valine, were chosen as strong candidates. Third, to achieve an efficient coupling, residues with a relatively high solvent accessibility were selected. The solvent accessibility of residues ranging from 0 (no accessibility) to 1 (full accessibility) was evaluated by the web-based program ASA-View.

Figure 2A:
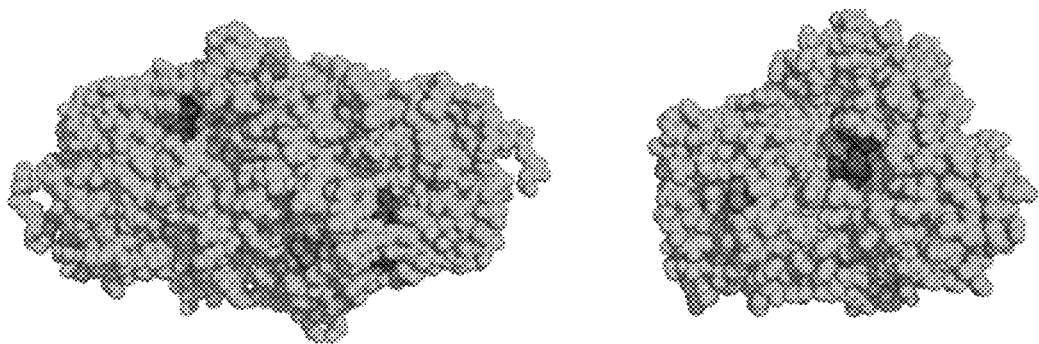
FIG. 2A schematically shows genetic incorporation of AZF (p-azido-L-phenylalanine). The dimeric form of FDH in complex with a cofactor (blue) shown as the left image in FIG. 2A is derived from the Protein Data Bank (PDB ID: 3WR5). The AZF conjugation site, V237 (valine at position 237), is highlighted in magenta. The MDH in complex with a cofactor (blue) shown as the right image in FIG. 2A is derived from the Protein Data Bank (PDB ID: 1LJ8). The AZF conjugation site, V417 (valine at position 417), is highlighted in magenta.

According to the previous studies by the inventors of the present disclosure, residues with an ASA value greater than 0.4 were suitable as a conjugation site. Based on these criteria, the valine at position 237 of FDH (0.423 ASA index) and the valine at position 417 of MDH (0.462 ASA index) were determined as coupling sites [see FIG. 2A].

Figure 5:
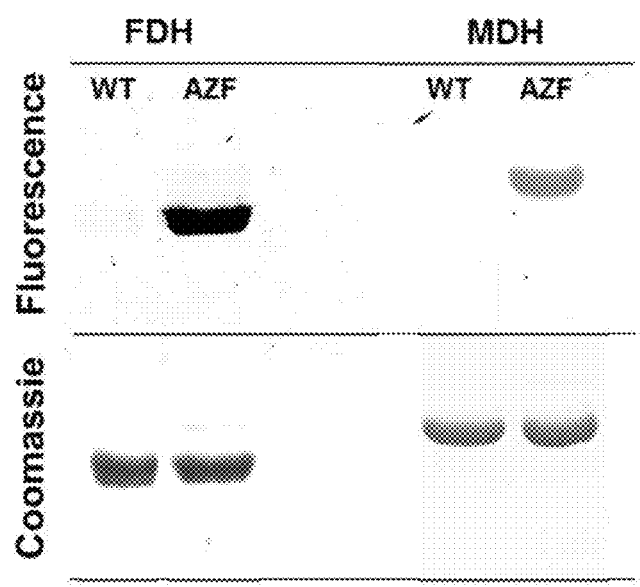
FIG. 5 shows a result of in-gel fluorescence analysis of FDH prepared in Example 1 (FDH-WT), wild-type MDH (MDH-WT) and their variants (FDH-AZF and MDH-AZF) upon reaction with DBCO-PEG$_4$-carboxyrhodamine.

Site-specific genetic incorporation of AZF was performed by the introduction of an amber codon into the predetermined sites of FDH- and MDH-encoding genes. Host cells were induced to express an orthogonal pair of amber suppressor tRNA and tRNA synthetase as well as the target gene in the presence of AZF in a culture medium. The expression yield of AZF-bearing FDH and MDH was 5 and 8 $mgL^{-1}$, respectively. Purified FDH and MDH variants were analyzed by dye labeling and mass spectrometry to verify the bioorthogonal reactivity and site-specific incorporation of AZF, respectively. In contrast to the wild-type FDH (FDH-WT) and MDH (MDH-WT) that did not show fluorescence when mixed with a DBCO (dibenzocyclooctyne)-functionalized fluorescence dye, the variants exhibited strong fluorescence [see FIG. 5].

Figure 2B:
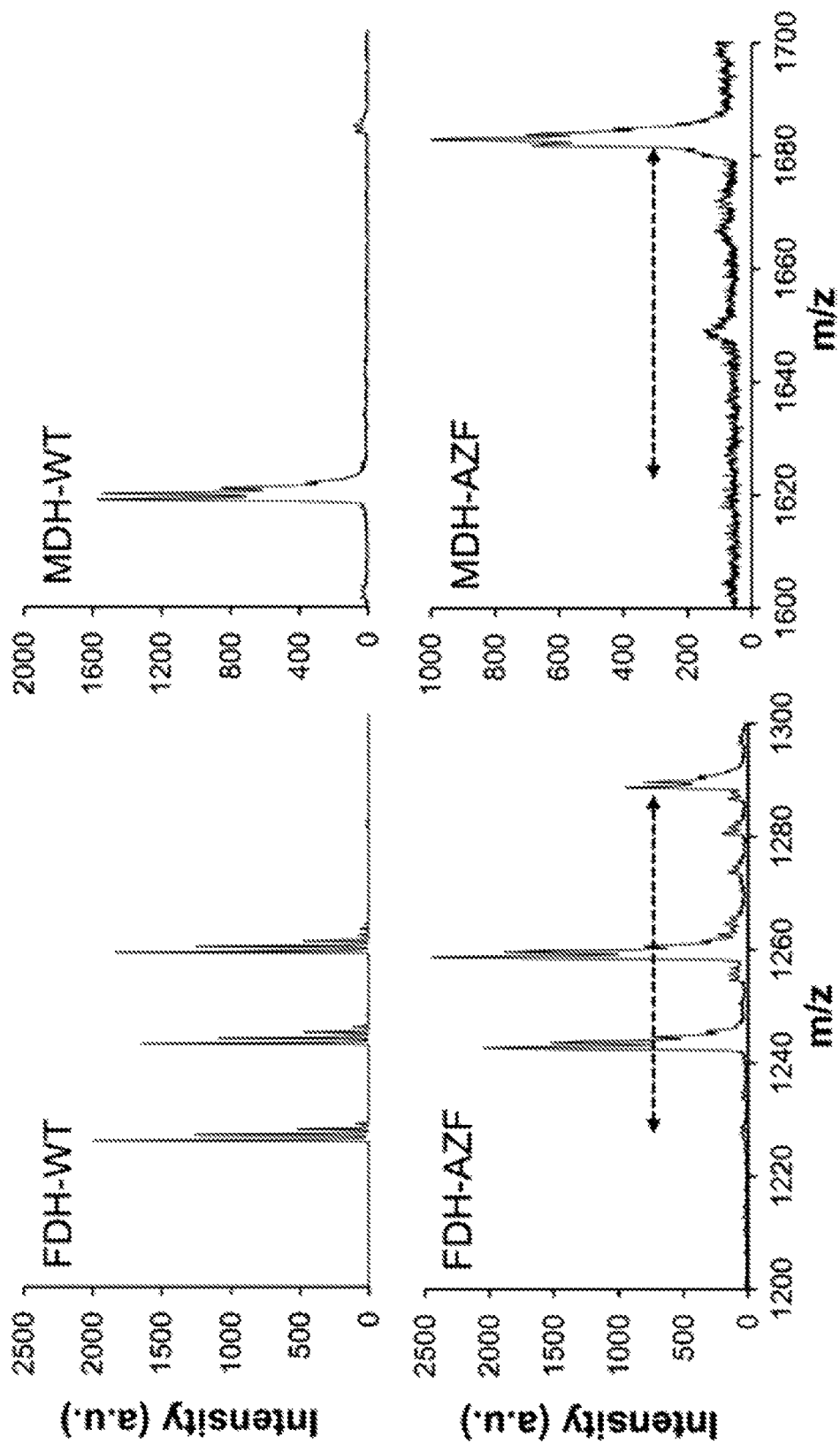
FIG. 2B shows a MALDI-TOF mass spectrometry result for wild-type FDH (FDH-WT), wild-type MDH (MDH-WT) and their variants (FDH-AZF and MDH-AZF).
Figure 4A:
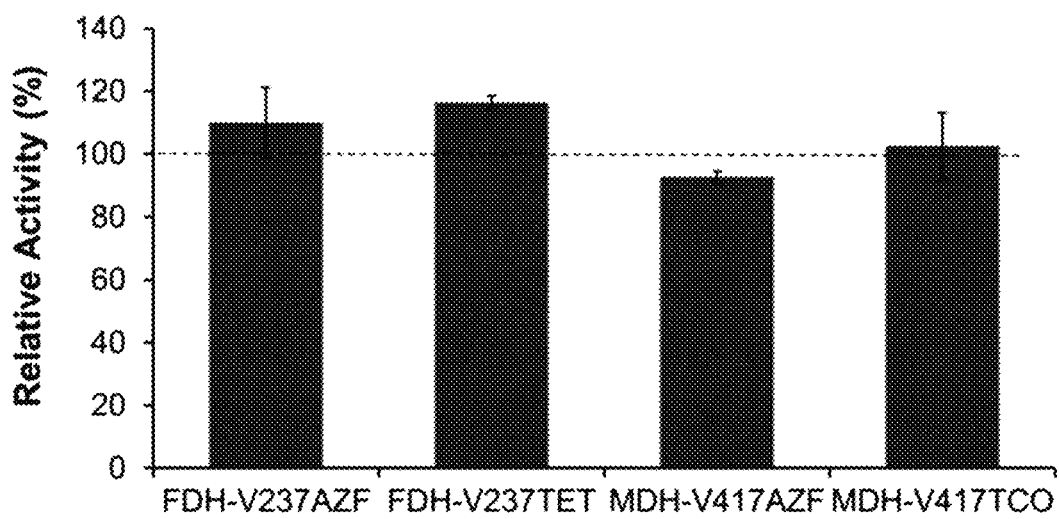
FIGS. 4A-4B show the enzymatic activity of a FDH-MDH conjugate synthesized in Example 3.

The MALDI-TOF mass spectra of tryptic fragments demonstrated the high-fidelity incorporation of AZF in response to the amber codons at position 237 for FDH and position 417 for MDH [see FIG. 2B]. To investigate the effect of AZF incorporation on the native activity, the variants were subjected to an enzymatic activity assay in comparison to the wild-type enzymes [see FIG. 4A]. Both variants containing AZF (FDH-AZF and MDH-AZF) retained enzymatic activities comparable to that of their respective wild types.

Figure 3A:
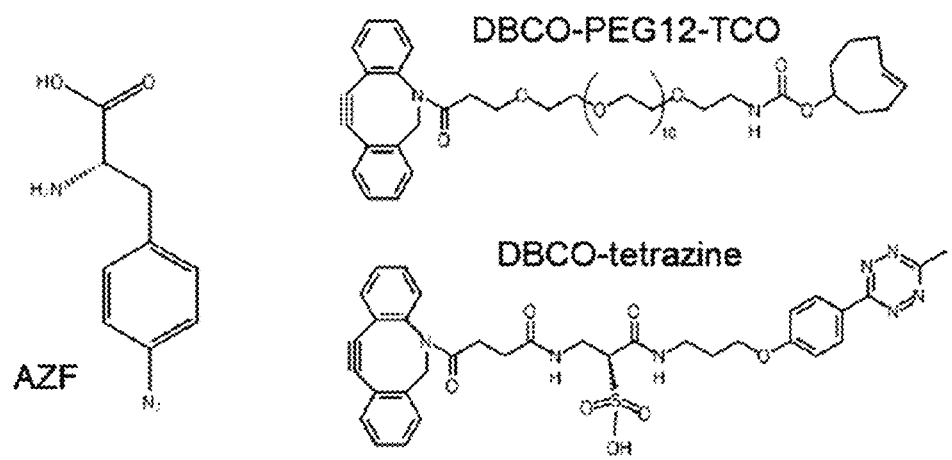
FIGS. 3A-3C schematically show a process of synthesizing a FDH-MDH conjugate in Example 3 and size characterization of a FDH-MDH conjugate synthesized in Example 3 and wild-type FDH (FDH-WT) and wild-type MDH (MDH-WT) prepared in Example 1.
Figure 3B:
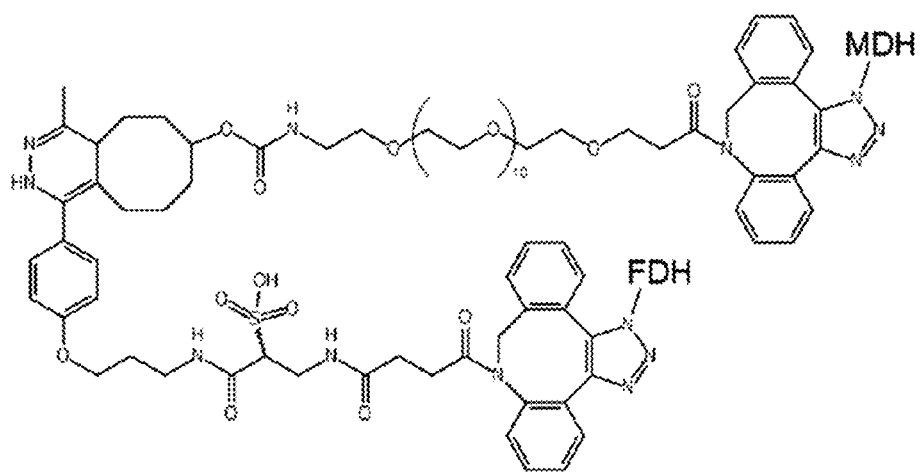

Because genetically encoded AZFs have been found to be situated at chemically well-defined positions and have bioorthogonal reactivity towards SPAAC, the variants of FDH and MDH provide a modular platform to generate FDH-MDH conjugates through a chemical linker. To cross-link FDH-AZF to MDH-AZF, FDH-AZF was reacted with a DBCO-tetrazine linker through SPAAC to generate FDH-TET, and was desalted to remove residual linkers. Likewise, MDH-AZF was conjugated to a DBCO-$PEG_{12}$-TCO linker to generate MDH-TCO [see FIG. 3A]. The majority of catalytic activity of each enzyme was retained even after the linker conjugation [FIG. 4A]. A second bioorthogonal reaction, IEDDA, was carried out to covalently link FDH-TET to MDH-TCO to generate the FDH-MDH conjugate [see FIG. 3B].

Figure 3C:
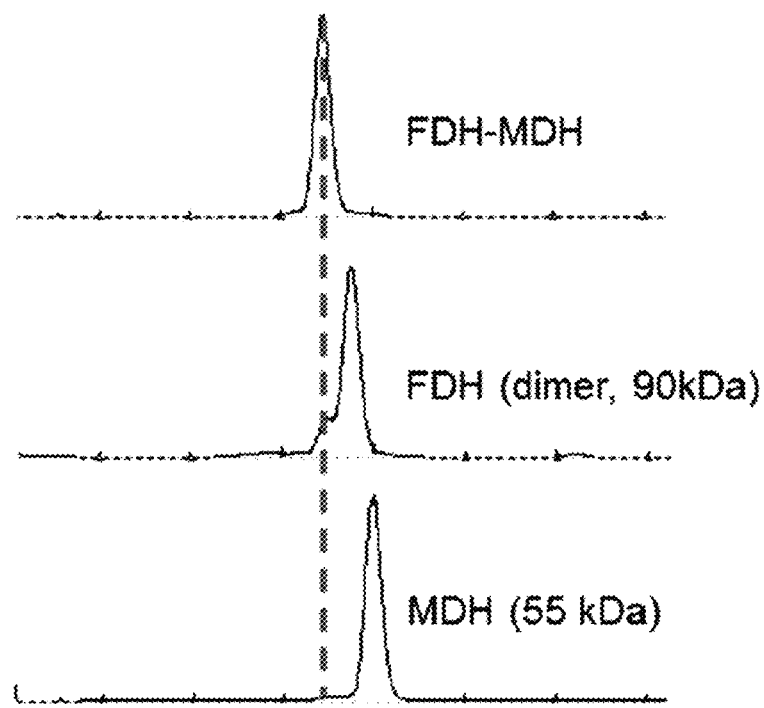
Figure 6:
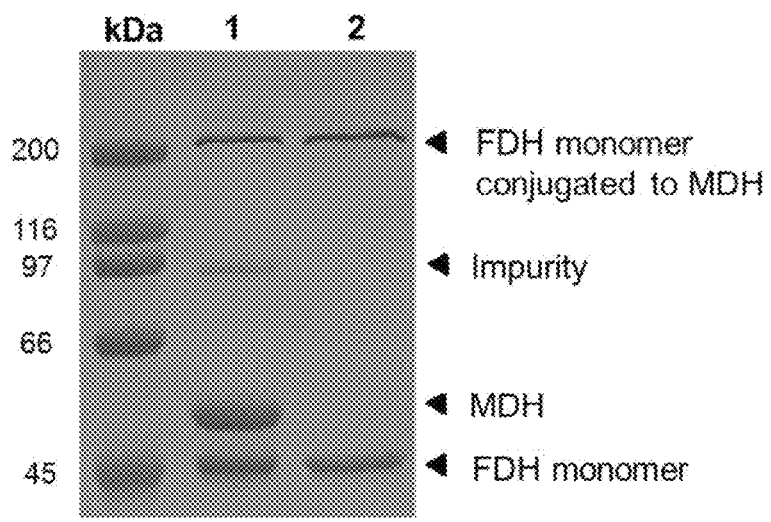
FIG. 6 shows a result of SDS-PAGE analysis of a FDH-MDH conjugate synthesized in Example 3 (FDH monomer to conjugated to MDH), an impurity, MDH and a FDH monomer [lane 1: conjugation reaction mixture; lane 2: purified FDH-MDH conjugate].

In SDS-PAGE analysis of the reaction mixture, a single band slightly larger than the 200-kDa standard protein was detected [see FIG. 6], indicating that the FDH-TET reacted with MDH-TCO to form FDH-MDH. A slower migration than expected from the total molecular weight of the monomeric FDH-MDH conjugate, 110 kDa, resulted from the long and flexible PEG spacer, which retarded mobility through the gel matrix. The FDH-MDH conjugate was isolated from the reaction mixture by performing anion exchange chromatography. Because the FDH dimer dissociated in the SDS-PAGE, two discrete bands were resolved with the upper band corresponding to the monomeric FDH conjugated to MDH, while the lower band showed the same molecular weight with the unmodified monomeric FDH [see FIG. 6]. An apparent size increase upon FDH-MDH conjugation was confirmed in comparison to the dimeric FDH and MDH by size exclusion chromatography [see FIG. 3C]. The conjugate exhibited a sharp and symmetric peak with an elution time earlier than its parents without any detectable impurity, indicating its high homogeneity and purity. The reaction yield at each step of the conjugate synthesis is summarized in Table 1.

TABLE 1

| Step | Purification | FDH (mg) | Yield (%) | MDH (mg) | Yield (%) |
|---|---|---|---|---|---|
| Bacterial expression | Ni-NTA affinity | 2.0$^a$ | 100 | 2.0$^b$ | 100 |
| Linker conjugation by SPAAC | Desalting | 1.9$^c$ | 95 | 1.8$^d$ | 90 |
| Protein conjugation by IEDDA reaction | Anion exchange | 0.54$^e$ | 27 | 0.33$^f$ | 17 |

Due to the dimeric nature of FDH, however, the FDH-MDH conjugate may display two different configurations, i.e., a single MDH attached to either subunit of a dimeric FDH or double MDHs attached to both subunits. To examine its organization, the formate oxidation activity and the D-mannitol reduction activity of the FDH-MDH conjugate were individually measured and then fitted to respective linear functions that relate enzymatic activities to molar concentrations. The FDH-MDH conjugate solution was found to have the formate oxidation activity corresponding to 5.6 mM of monomeric FDH-AZF, i.e., 2.8 mM of dimeric FDH-AZF, and the D-fructose reduction activity corresponding to 2.5 mM of MDH-AZF, demonstrating that the 2:1 molar species, i.e., dimeric FDH-AZF cross-linked to single MDH-AZF, was dominant over the 1:1 molar species.

Figure 4B:
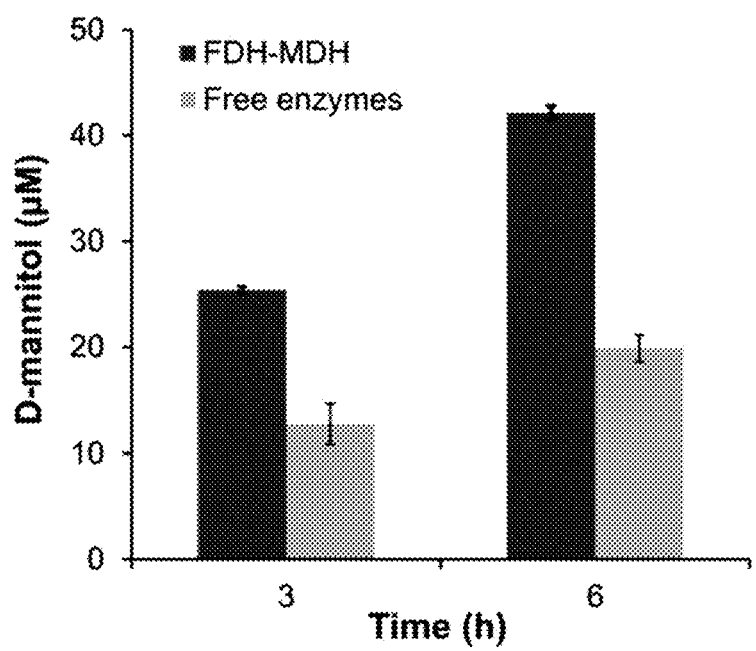
Figure 8A:
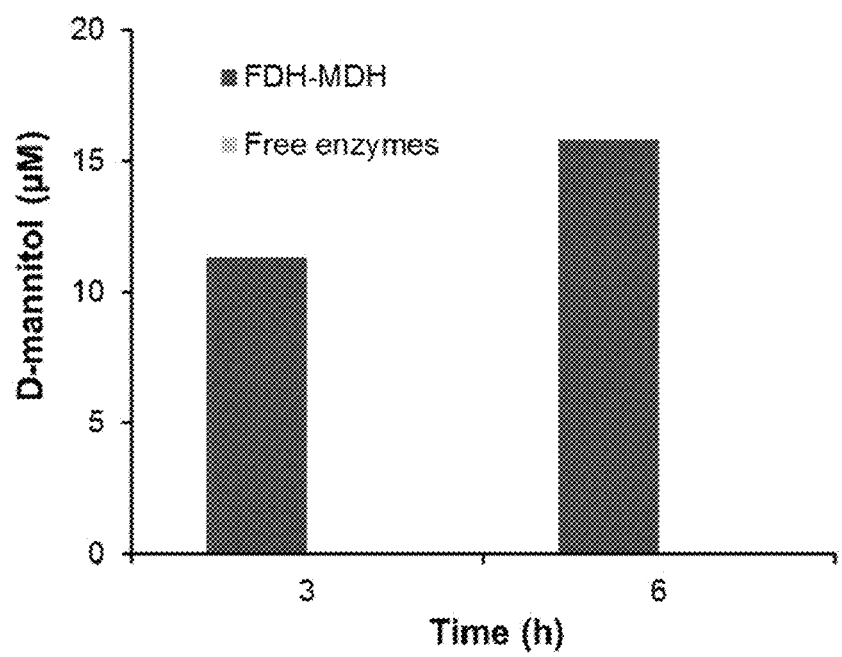
FIGS. 8A-8B show mannitol production by a FDH-MDH conjugate synthesized in Example 3 or free enzymes.
Figure 8B:
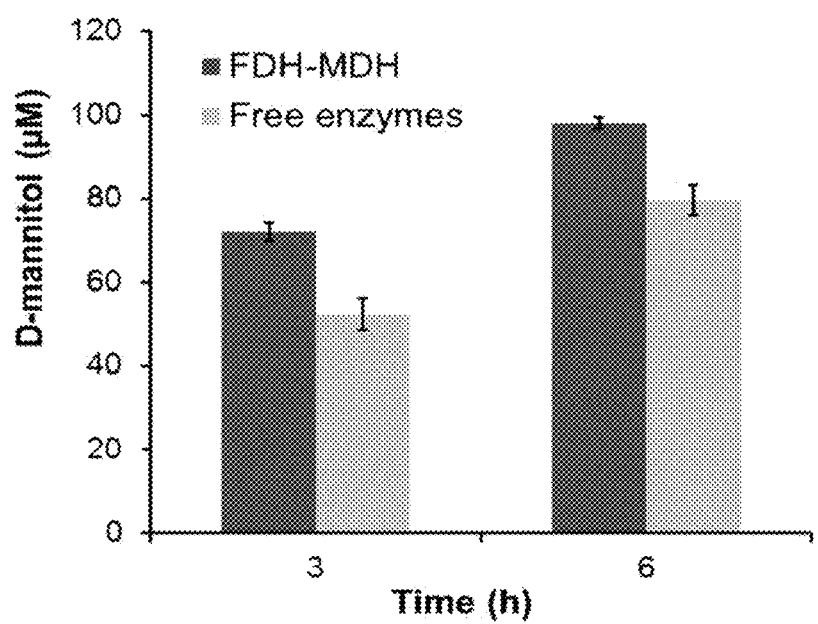

In the presence of a saturating amount of the substrates D-fructose and formate, an efficient transfer of NADH generated by FDH to the active site of MDH is a rate-limiting step in the enzymatic production of D-mannitol [see FIG. 10]. To investigate the importance of multi-enzyme conjugation on NADH transport, the multi-enzyme cascade reaction was conducted without agitation in the presence of either the FDH-MDH conjugate at a concentration corresponding to 5 nM MDH-AZF or a free enzyme mix of FDH-WT (5.5 nM as a dimer) and MDH-WT (5 nM) as well as an excess of substrates and NAD$^+$. A low concentration of enzymes and the absence of turbulent stirring should create a locally diffusion-controlled cascade reaction system in which inter-enzyme transport of NADH should determine the rate of mannitol production, thereby facilitating the observation of enhanced catalytic performance contributed by site-specific enzyme tethering. Samples taken at 3 and 6 hours after the initiation of reaction were withdrawn from the reaction solution and subjected to the D-mannitol assay, and absorbance changes at 340 nm were used to estimate the mannitol concentration by interpolation. The actual D-mannitol concentrations in the samples were obtained by multiplying the dilution factor 5 to yield FIG. 4 [see FIG. 7]. In the presence of the FDH-MDH conjugate, 25 mM D-mannitol was produced for 3 hours compared to only 13 mM with free enzymes [see FIG. 4B]. At 6 hours, a similar trend was observed. In the presence of the FDH-MDH conjugate and free enzymes, 42 and 20 mM of D-mannitol were detected, respectively. The apparently higher reaction efficiency of the FDH-MDH conjugate over unconjugated enzymes can be attributed to proximity channeling of NADH between the two enzymes, when there is no stirring for thorough mixing of components in the reaction solutions. Regardless of the enzyme concentrations, the conjugated FDH has the subsequent enzyme MDH in proximity within the spatial radius set by the chemical linker. The proximity effect by the enzyme conjugation, in comparison to free enzymes, became more pronounced when the intermolecular distance was greater [see FIG. 8A], or lessened at a higher concentration of enzymes [see FIG. 8B]. To summarize, these results clearly demonstrated that multiple enzymes were conjugated at specific sites with retained activities, and the enzyme conjugate showed the enhanced catalytic efficiency over free enzymes by proximity-enhanced NADH processing.

In the present disclosure, a method to construct the multi-enzyme reaction system using two orthogonal click reactions (SPAAC and IEDDA) as well as site-specific incorporation of a non-natural amino acid (AZF) was completed. The introduction of a SPAAC-clickable azido group to permissive sites of FDH and MDH serves as a chemical handle for IEDDA-clickable linker conjugation. Then, the two enzyme-linker conjugates are connected via an IEDDA click reaction. The multi-enzyme conjugate (FDH-MDH conjugate) was successfully isolated through standard chromatographic protein purification procedures. The FDH-MDH conjugate exhibited an enhanced D-mannitol production rate compared to free FDH and MDH likely due to cofactor shuttling between FDH and MDH. Because the technique and strategy described here are very general, they would be applicable to the conjugation of other multiple enzymes, aiming for enhanced catalytic properties. More broadly, this strategy would enable a convenient protein-to-protein conjugation without significant perturbations of protein conformation.

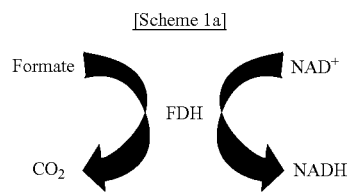

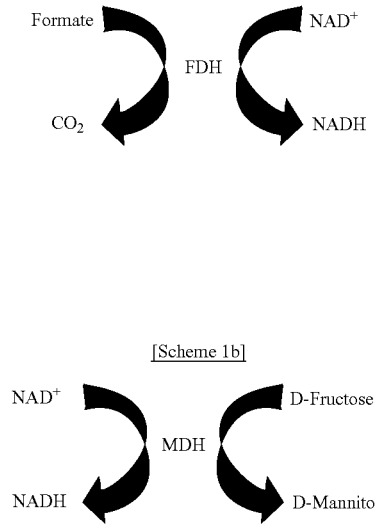

What is claimed is:

1. A method for synthesizing an organic compound, comprising a step of performing a multi-enzyme cascade reaction using a multi-enzyme conjugate, wherein
the multi-enzyme conjugate has the following structure:

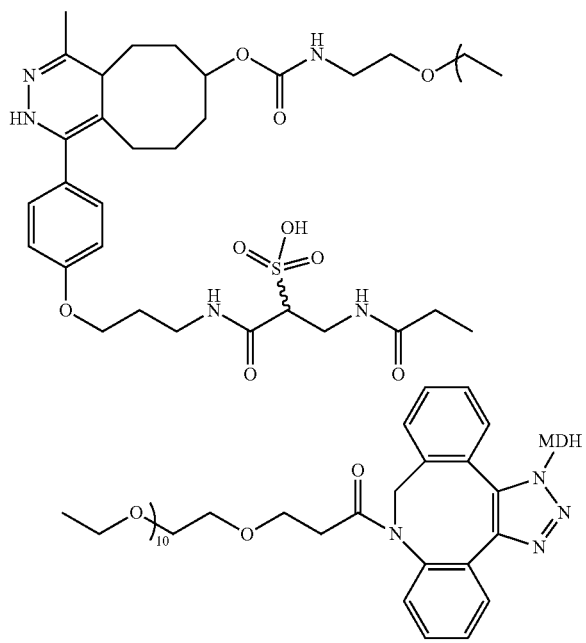

where FDH is a formate dehydrogenase obtained from *Thiobacillus* sp. KNK65MA, and MDH is a mannitol-2-dehydrogenase obtained from *Pseudomonas fluorescens*, the multi-enzyme cascade reaction comprises a first enzymatic reaction and a second enzymatic reaction, a product of the first enzymatic reaction is used as a reactant of the second enzymatic reaction, the first enzyme of the multi-enzyme conjugate acts as a biocatalyst of the first enzymatic reaction, and the second enzyme of the multi-enzyme conjugate acts as a biocatalyst of the second enzymatic reaction.

2. The method for synthesizing an organic compound according to claim 1, wherein the first enzymatic reaction and the second enzymatic reaction are a pair selected from the following reaction pairs: